US009248124B2

(12) United States Patent
Adams et al.

(10) Patent No.: US 9,248,124 B2
(45) Date of Patent: Feb. 2, 2016

(54) USE OF INHIBITORS OF IκB KINASE FOR THE TREATMENT OF CANCER

(75) Inventors: Julian Adams, Boston, MA (US); Kenneth C. Anderson, Wellesley, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 10/495,041

(22) PCT Filed: Nov. 6, 2002

(86) PCT No.: PCT/US02/35645
§ 371 (c)(1),
(2), (4) Date: Oct. 12, 2004

(87) PCT Pub. No.: WO03/039545
PCT Pub. Date: May 15, 2003

(65) Prior Publication Data
US 2005/0049265 A1 Mar. 3, 2005

Related U.S. Application Data

(60) Provisional application No. 60/344,911, filed on Nov. 7, 2001.

(51) Int. Cl.
*A61K 31/54* (2006.01)
*A61K 31/44* (2006.01)

(52) U.S. Cl.
CPC ..................................... *A61K 31/44* (2013.01)

(58) Field of Classification Search
USPC .................... 514/232.8, 292, 227.8, 227.5
See application file for complete search history.

(56) References Cited

U.S. PATENT DOCUMENTS 6,123,943 A * 9/2000 Baba et al. ..................... 424/773
6,248,326 B1 * 6/2001 Blair et al. ................. 424/139.1
(Continued)

FOREIGN PATENT DOCUMENTS

DE 19807993 A1 9/1999
DE 19951360 A1 5/2001
(Continued)

OTHER PUBLICATIONS

Goodman &Gilman's, The Pharmacological Basis of Therapeutics, Ninth Edition, (1996), Calabresi et al., Section X, Chemotherapy of Neoplastic Diseases, pp. 1225-1229.*
(Continued)

Primary Examiner — San-Ming Hui
(74) Attorney, Agent, or Firm — Millennium Pharmaceuticals, Inc.

(57) ABSTRACT

The present invention provides inhibitors of IκB kinase of general formula (I).

(I)

or a stereoisomer or physiologically tolerable salt thereof, for use in the inhibition of the growth of a multiple myeloma cell and for use in the treatment of multiple myeloma, wherein $R^1$-$R^8$ and $B_6$-$B_9$ are described in the specification.

4 Claims, 11 Drawing Sheets

(56) References Cited

U.S. PATENT DOCUMENTS

| | | | |
|---|---|---|---|
| 6,627,637 B2* | 9/2003 | Ritzeler et al. | 514/292 |
| 7,026,331 B2 | 4/2006 | Ritzeler et al. | |
| 7,348,336 B2 | 3/2008 | Ritzeler et al. | |
| 2002/0099068 A1 | 7/2002 | Ritzeler et al. | |
| 2005/0049265 A1* | 3/2005 | Adams | 514/267 |
| 2006/0166978 A1 | 7/2006 | Ritzeler et al. | |

FOREIGN PATENT DOCUMENTS

| | | |
|---|---|---|
| GB | 2303627 A | 2/1997 |
| WO | WO 99/65449 A2 | 12/1999 |
| WO | 0168648 * | 9/2001 |
| WO | WO 01/68648 A1 | 9/2001 |

OTHER PUBLICATIONS

ACS: What is Multiple Myeloma? Cancer Reference Information, www.cancer.org (2006), printed pp. 1 and 2.*

Feinman et al, Role of NF—kappa-Beta in the Rescue of Multiple Myeloma Cells From Glucocorticoid-Induced Apoptosis by Bcl-2, Blood, vol. 93 No. 9 May 1, 1999: pp. 3044-3052.*

Hideshima , T. The Proteasome Inhibitor PS-341 Inhivits Growth, Induces Apoptosis, and Overcomes Drug Resistance in Human Multiple Myeloma Cells, Cancer Research 61, 3071-3076, Apr. 2001.*

Borset et al. Apoptosis, proliferation and NF-kappaB activation induced by agonistic Fas antibodies in the human myeloma cell line OH-2:amplification of Fas-mediated apoptosis by tumor necrosis factor. 1996. Eur J. Hematology. Abstract.*

Feinman et al., Blood, 1999;93(9):3044-3052.*

Kobayashi, Jun'ichi, et al., "Eudistomins A, D, G, H, I, J, M, N, O, P, and Q, Bromo-, Hydroxy-, Pyrrolyl-, and 1-Pyrrolinyl-β-carbolines from the Antiviral Caribbean Tunicate *Eudistoma olivaceum*," *Journal of the American Chemical Society*, vol. 106, No. 5 (1984) pp. 1526-1528.

Rinehart, Kenneth L., et al., "Eudistomins C, E, K, and L, Potent Antiviral Compounds Containing a Novel Oxathiazepine Ring from the Caribbean Tunicate *Eudistoma olivaceum*," *Journal of the American Chemical Society*, vol. 106, No. 5 (1984) pp. 1524-1526.

Anderson, K.C., "Novel Biologically Based Therapies for Myeloma," Cancer Journal, 7 Supplement, No. 1 (Jul.-Aug. 2001) pp. S19-S23.

Hideshima, Teru, et al., "The Proteasome Inhibitor PS-341 Inhibits Growth, Induces Apoptosis, and Overcomes Drug Resistance in Human Multiple Myeloma Cells," Cancer Research, vol. 61 (Apr. 1, 2001) pp. 3071-3076.

Hideshima, Teru, et al., "Novel Therapies Targeting the Myeloma Cell and Its Bone Marrow Microenvironment," Seminars in Oncology, vol. 28, No. 6 (Dec. 2001) pp. 607-612.

Hideshima, Teru, et al., "NF-KB as a Therapeutic Target in Multiple Myeloma," The Journal of Biological Chemistry, vol. 2771 No. 19 (May 10, 2002) pp. 16639-16647.

Hideshima, Teru, et al., "MLN120B, A Novel IKB Kinase B Inhibitor, Blocks Multiple Myeloma Cell Growth in vitro and in vivo," Clinical Cancer Research vol. 12(19) (Oct. 1, 2006) pp. 5887-5894.

Nagashima Kumiko, at al., "Rapid TNFR1-Dependent Lymphocyte Depletion In Vivo With a Selective Chemical Inhibitor of IKKB," Blood, vol. 107, No. 11 (Jun. 1, 2006) pp. 4266-4273.

* cited by examiner

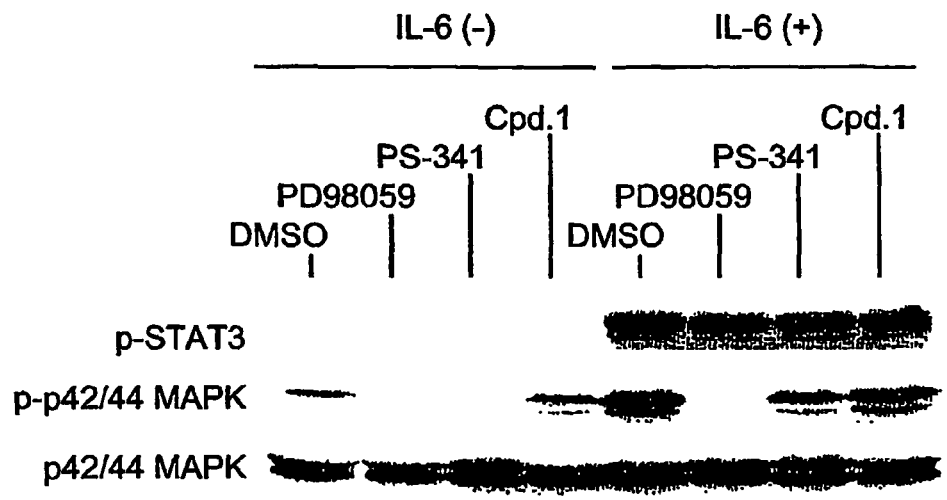
FIG. 5
FIG. 6A
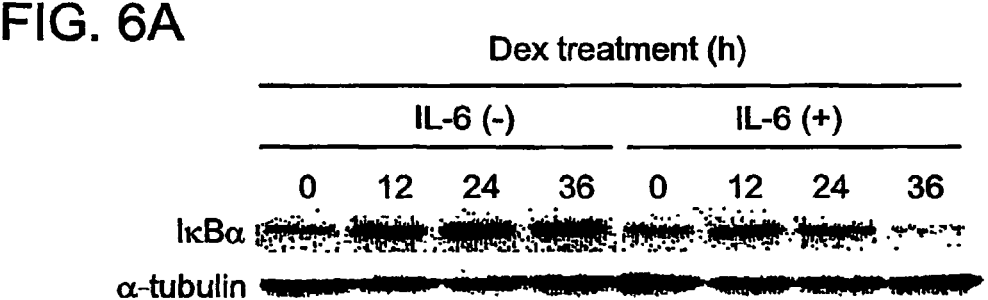
FIG. 6B
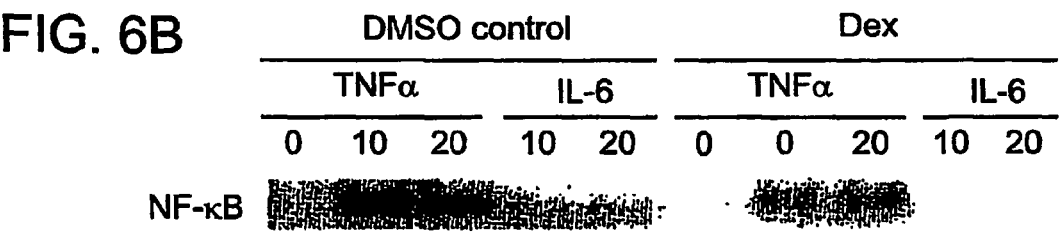
FIG. 6C
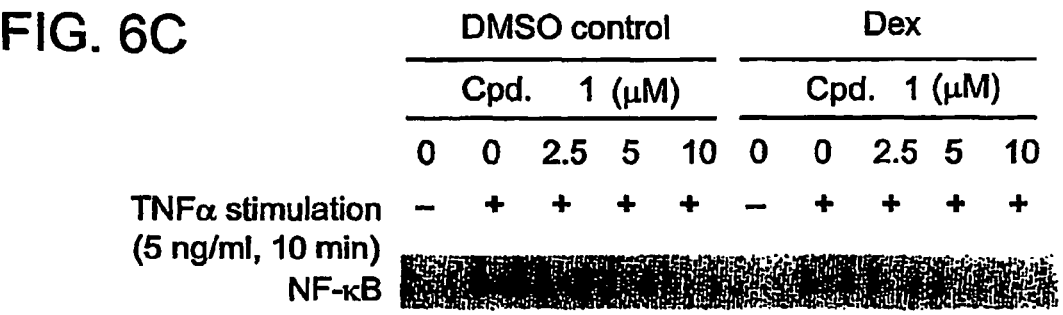

USE OF INHIBITORS OF IκB KINASE FOR THE TREATMENT OF CANCER

BACKGROUND OF THE INVENTION

1. Field of the Invention

This invention relates to the treatment of cancer. In particular, the invention relates to the use of inhibitors IκB kinase to inhibit the growth of a cancer cell and for the treatment of cancer, including multiple myeloma.

2. Background of the Invention

The transcription factor NF-κB is a member of the Rel protein family, and is typically a heterodimer composed of p50 and p65 subunits. NF-κB is constitutively present in the cytosol, and is inactivated by its association with one of the IκB family of inhibitors. Palombella et al., WO 95/25533, teaches that the ubiquitin-proteasome pathway plays an essential role in the regulation of NF-κB activity, being responsible both for processing of p105 to p50 and for the degradation of the inhibitor protein IκBα. Chen et al., *Cell* 84:853 (1996), teaches that prior to degradation, IκBα undergoes selective phosphorylation at serine residues 32 and 36 by the multisubunit IκB kinase complex (IKK). Once phosphorylated, IκB is targeted for ubiquitination and degradation by the 26S proteasome, allowing translocation of NF-κB into the nucleus, where it binds to specific DNA sequences in the promoters of target genes and stimulates their transcription.

Ritzeler et al., WO 01/68648, discloses a series of beta-carboline compounds with IκB kinase inhibitory activity. Rinehart et al., U.S. Pat. No. 4,631,149, discloses beta-carboline compounds useful as antiviral, antibacterial, and anti-tumor agents.

The protein products of genes under the regulatory control of NF-κB include cytokines, chemokines, cell adhesion molecules, and proteins mediating cellular growth and control. Importantly, many of these proinflammatory proteins also are able to act, either in an autocrine or paracrine fashion, to further stimulate NF-κB activation. In addition, NF-κB plays an important role in the growth of normal and malignant cells. Baldwin, *J. Clin. Invest.*, 107:241 (2001), teaches that NF-κB promotes cell growth by upregulating cyclin D transcription, with associated hyperphosphorylation of Rb, G1 to S-phase transition, and inhibition of apoptosis. Bargou et al., *J. Clin. Invest.*, 100:2961 (1997), teaches that NF-κB is constitutively activated in Hodgkin's disease, and inhibition of NF-κB blocks growth of these lymphoma cells. Furthermore, Mayo et al., *Science* 178:1812 (1997), teaches that inhibition of NF-κB via expression of the super-repressor of IκBα induces apoptosis in cells expressing the oncogenic allele of H-Ras.

Read et al., *Immunity* 2:493-506 (1995), teaches that proteasome-mediated activation of NF-κB is required for expression of cell adhesion molecules, such as E-selectin, ICAM-1, and VCAM-1. Zetter, *Seminars in Cancer Biology* 4:219-229 (1993), teaches that cell adhesion molecules are involved in tumor metastasis and angiogenesis in vivo, by directing the adhesion and extravastation of tumor cells to and from the vasculature to distant tissue sites within the body. Moreover, Beg and Baltimore, *Science* 274:782 (1996), teaches that NF-κB is an anti-apoptotic controlling factor, and that inhibition of NP-κB activation makes cells more sensitive to environmental stress and cytotoxic agents.

Multiple myeloma is a B-cell malignancy of the plasma cells. It represents the second most common hematological malignancy, with non-Hodgkin's lymphoma being the most common. The annual incidence in the United States (US) is about four per 100,000, and rates in northern Europe are similar to the US. Greenlee et al., *CA Cancer J Clin* 50:7-33 (2000) discloses that approximately 13,600 cases of multiple myeloma are diagnosed each year with ~11,200 deaths per year due to the disease, representing ~2% of all cancer deaths. Multiple myeloma is one of only three cancer types to show increased mortality rates for both men and women (increases of 5.6 and 3.8%, respectively) during the period 1991-1995.

Multiple myeloma results from the clonal proliferation of plasma cells arising in the lymph nodes and "homing" to the bone marrow where these cells localize and proliferate. The disease is characterized by marrow plasma cell tumors and overproduction of a patient-specific intact monoclonal immunoglobulin heavy and/or light chain (paraprotein or M-protein). Plasma cell tumors produce immunoglobulin G (IgG) in about 53% of myeloma patients and immunoglobulin A (IgA) in about 25%; 40% of these IgG and IgA patients also have Bence Jones proteinuria. Light chain myeloma is found in 15 to 20% of patients; their plasma cells secrete only free monoclonal light chains (κ or λ Bence Jones protein), and serum M-components are usually absent on electrophoresis. Immunoglobulin D (IgD) myeloma accounts for about 1% of cases. Only a few cases of immunoglobulin E (IgE) myeloma have been reported. The production of an easily detectable paraprotein in the blood and/or urine is a convenient marker for the tumor burden in most of these patients.

Multiple myeloma, unless successfully treated, leads to progressive morbidity and eventual mortality by lowering resistance to infection and causing significant skeletal destruction (with bone pain, pathological fractures, and hypercalcemia), anemia, renal failure, and, less commonly, neurological complications and hyperviscosity. Anderson et al., *Semin. Hematol.* 36:3 (1999), teaches that patients may initially respond to cytotoxic chemotherapy and/or steroids, but they ultimately suffer from resistant disease. This cancer remains incurable. Raje and Anderson, *New Eng J Med* 341: 1606-1609 (1999) states that the five-year survival rate for patients with multiple myeloma has remained at 29% "for more than four decades".

Vidriales M B and Anderson K C, *Molec. Med. Today* 2(1):425-431 (1996), suggests that there are complex controls on the growth of the myeloma tumor cell mass in the bone marrow, with influences from the microenvironment of the bone marrow and the production of cytokines by the malignant cell and bone marrow stromal cells. IL-6 is a critical growth factor for the myeloma cell and also inhibits apoptosis in myeloma cells. Chauhan et al., *Blood*, 87:1104 (1996), teaches that adhesion of myeloma cells to the bone marrow stromal cells (BMSCs) induces NF-κB dependent upregulation of IL-6 transcription and perpetuates further myeloma cell proliferation. Furthermore, Hideshima et al., *Oncogene* 20:4519 (2001), teaches that multiple myeloma cells secrete TNFα, which induces activation of NF-κB in BMSCs, and thereby directly upregulates IL-6 transcription and secretion in BMSCs. The reference also teaches that TNFα-induced NF-κB activation results in upregulation of ICAM-1 (CD54) and VCAM-1 (CD106) expression on both MM cells and BMSCs, resulting in an increase in MM-BMSC binding. Consistent with the role for NF-κB in multiple myeloma suggested by these references, Feinman R et al., *Blood* 93:3044 (1999) teaches that elevated levels of NF-κB activity are found in relapsing multiple myeloma.

Thus, there remains a need to identify inhibitors of NF-κB that are effective for the treatment of cancer, including multiple myeloma.

BRIEF SUMMARY OF THE INVENTION

The present inventors have discovered that specific inhibition of IκB kinase (IKK) inhibits cancer cell growth, inhibits the NF-κB-mediated upregulation of adhesion molecule expression on cancer cells, and inhibits intercellular adhesion. Furthermore, inhibition of IKK blocks the protective effect of IL-6 against drug-induced apoptosis.

In a first aspect therefore, the invention provides methods for inhibiting cancer cell growth, comprising contacting a cancer cell with an inhibitor of IκB kinase as described herein. In a first embodiment, the inhibitor of IκB kinase is a compound of formula (I)

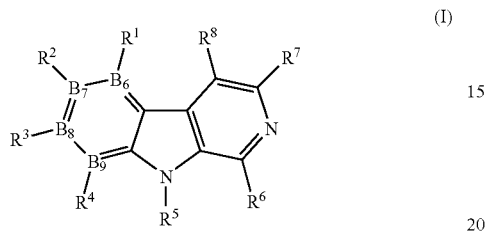

or a stereoisomer or physiologically tolerable salt thereof, wherein:

$B_6/B_7$, $B_8$, and $B_9$ are independently selected from the group consisting of carbon atom and nitrogen atom, where a total of no more than two of $B_6$, $B_7$, $B_8$, and $B_9$ are nitrogen atoms; and in case a):
the substituents $R^1$, $R^2$ and $R^3$ independently of one another are
1.1. hydrogen atom,
1.2. halogen,
1.3. —CN,
1.4. —COOH,
1.5. —NO$_2$,
1.6. —NH$_2$,
1.7. —O—(C$_1$-C$_{10}$)-alkyl, wherein alkyl is unsubstituted or mono- to penta-substituted with a substituent or substituents independently selected from the group consisting of
  1.7.1 phenyl, which is unsubstituted or mono- to penta-substituted by halogen or —O—(C$_1$-C$_4$)-alkyl,
  1.7.2 halogen,
  1.7.3 —NH$_2$,
  1.7.4 —OH,
  1.7.5 —COOR$^{16}$, wherein R$^{16}$ is hydrogen atom or —(C$_1$-C$_{10}$)-alkyl,
  1.7.6 —NO$_2$,
  1.7.7 —S(O)$_y$—R$^{14}$, wherein y is zero, 1 or 2, and R$^{14}$ is —(C$_1$-C$_{10}$)-alkyl, phenyl, which is unsubstituted or mono- to penta-substituted with a substituent or substituents independently selected from the group defined under 1.7.1 to 1.7.11, amino or —N(R$^{13}$)$_2$, wherein each R$^{13}$ independently is hydrogen atom, phenyl, —(C$_1$-C$_{10}$)-alkyl, —C(O)—(C$_1$-C$_7$)-alkyl, —C(O)-phenyl, —C(O)—NH—(C$_1$-C$_7$)-alkyl, —C(O)—O-phenyl, —C(O)—NH-phenyl, —C(O)—O—(C$_1$-C$_7$)-alkyl, or —S(O)$_y$—R$^{14}$ wherein R$^{14}$ and y are as defined above, and wherein alkyl or phenyl in each case is unsubstituted or mono- to penta-substituted with a substituent or substituents independently selected from the group defined under 1.7.1 to 1.7.11, or the two R$^{13}$ groups, together with the nitrogen atom to which they are bonded, form a heterocycle having 5 to 7 ring atoms,
  1.7.8 —O-phenyl, wherein phenyl is unsubstituted or mono- to penta-substituted with a substituent or substituents independently selected from the group defined under 1.7.1 to 1.7.11,
  1.7.9 a radical selected from the group consisting of pyrroline, tetrahydropyridine, piperidine, piperazine, imidazoline, pyrazolidine, furan, morpholine, pyridine, pyridazine, pyrazine, oxolan, imidazoline, isoxazolidine, 2-isoxazoline, isothiazolidine, 2-isothiazoline, thiophene, and thiomorpholine,
  1.7.10 —(C$_3$-C$_7$)-cycloalkyl or
  1.7.11 =O,
1.8. —N(R$^{13}$)$_2$, wherein R$^{13}$ is as defined in 1.7.7 above,
1.9. —NH—C(O)—R$^{15}$, wherein R$^{15}$ is
  1.9.1 a radical selected from the group consisting of pyrrolidine, tetrahydropyridine, piperidine, piperazine, imidazoline, pyrazolidine, furan, morpholine, pyridine, pyridazine, pyrazine, oxolan, imidazoline, isoxazolidine, 2-isoxazoline, isothiazolidine, 2-isothiazoline, thiophene, and thiomorpholine,
  wherein said radical is unsubstituted or mono- to penta-substituted with a substituent or substituents independently selected from the group consisting of substituents defined under 1.7.1 to 1.7.11 above, —CF$_3$, benzyl, and —(C$_1$-C$_{10}$)-alkyl, wherein alkyl is unsubstituted or mono- to tri-substituted with a substituent or substituents independently selected from the group of substituents defined under 1.7.1 to 1.7.11 above,
  1.9.2 —(C$_1$-C$_{10}$)-alkyl, wherein alkyl is unsubstituted or mono- to penta-substituted with a substituent or substituents independently selected from the group consisting of substituents defined under 1.7.1 to 1.7.11 above and —O—(C$_1$-C$_{10}$)-alkyl, wherein alkyl is unsubstituted or mono- to penta-substituted with a substituent or substituents independently selected from the group of substituents defined under 1.7.1 to 1.7.11 above,
  1.9.3 —(C$_3$-C$_7$)-cycloalkyl,
  1.9.4 —N(R$^{13}$)$_2$, wherein R$^{13}$ is as defined in 1.7.7 above, or
  1.9.5 phenyl, wherein phenyl is unsubstituted or mono- to penta-substituted with a substituent or substituents independently selected from the group consisting of substituents defined under 1.7.1 to 1.7.11 above, —O—(C$_1$-C$_{10}$)-alkyl, —CN, —CF$_3$, and —(C$_1$-C$_{10}$)-alkyl, wherein alkyl is unsubstituted or mono- to tri-substituted with a substituent or substituents independently selected from the group of substituents defined under 1.7.1 to 1.7.11 above, or two substituents of the phenyl radical together form a dioxolane ring,
1.10. —S(O)$_y$—R$^{14}$, wherein R$^{14}$ and y are as defined in 1.7.7 above,
1.11. —C(O)—R$^{12}$, wherein R$^{12}$ is phenyl or —(C$_1$-C$_7$)-alkyl, wherein alkyl or phenyl are unsubstituted or mono- to penta-substituted with a substituent or substituents independently selected from the group of substituents defined under 1.7.1 to 1.7.11 above,
1.12. —C(O)—O—R$^{12}$, wherein R$^{12}$ is as defined in 11. above,
1.13. —(C$_1$-C$_{10}$)-alkyl, wherein alkyl is unsubstituted or mono- to penta-substituted with a substituent or substituents independently selected from the group of substituents defined under 1.7.1 to 1.7.11 above,
1.14. —O—(C$_1$-C$_6$)-alkyl-(C$_1$-C$_6$)-alkyl,
1.15. —O—(C$_0$-C$_4$)-alkyl-(C$_3$-C$_7$)-cycloalkyl, 1.16. —$(C_1$-$C_4)$-alkyl-$N(R^{13})_2$, wherein $R^{13}$ is as defined in 1.7.7 above
1.17. —$CF_3$ or
1.18. —$CF_2$—$CF_3$;

$R^4$ is
1. —$(C_1$-$C_{10})$-alkyl, wherein alkyl is unsubstituted or mono- to penta-substituted with a substituent or substituents independently selected from the group of substituents defined under 1.7.1 to 1.7.11 above,
2. —$CF_3$,
3. —$CF_2$—$CF_3$,
4. —CN,
5. —$S(O)_y$—$R^{14}$, wherein $R^{14}$ and y are as defined in 1.7.7 above,
6. —$NH_2$,
7. —O—$(C_1$-$C_{10})$-alkyl, wherein alkyl is unsubstituted or mono- to penta-substituted independently of one another by
  7.1 phenyl, which is unsubstituted or mono- to penta-substituted by halogen or —O—$(C_1$-$C_4)$-alkyl,
  7.2 halogen,
  7.3 —$NH_2$,
  7.4 —OH,
  7.5 —$COOR^{16}$, wherein $R^{16}$ is hydrogen atom or —$(C_1$-$C_{10})$-alkyl,
  7.6 —$NO_2$,
  7.7 —$S(O)_y$—$R^{14}$, wherein y is zero, 1 or 2, $R^{14}$ is —$(C_1$-$C_{10})$-alkyl, phenyl, which is unsubstituted or mono- to penta-substituted with a substituent or substituents independently selected from the group of substituents defined under 1.7.1 to 1.7.11 above, amino, and —$N(R^{13})_2$, wherein each $R^{13}$ independently is hydrogen atom, phenyl, —$(C_1$-$C_{10})$-alkyl, —C(O)—$(C_1$-$C_7)$-alkyl, —C(O)-phenyl, —C(O)—NH—$(C_1$-$C_7)$-alkyl, —C(O)—O-phenyl, —C(O)—NH-phenyl, —C(O)—O—$(C_1$-$C_7)$-alkyl, or —$S(O)_y$—$R^{14}$, wherein $R^{14}$ and y are as defined above, and wherein alkyl or phenyl in each case is unsubstituted or mono- to penta-substituted with a substituent or substituents independently selected from the group defined under 1.7.1 to 1.7.11, or the two $R^{13}$ groups, together with the nitrogen atom to which they are bonded, form a heterocycle having 5 to 7 ring atoms,
  7.8 —O-phenyl, wherein phenyl is unsubstituted or mono- to penta-substituted with a substituent or substituents independently selected from the group of substituents defined under 1.7.1 to 1.7.11 above,
  7.9 a radical selected from the group consisting of pyrrolidine, tetrahydropyridine, piperidine, piperazine, imidazoline, pyrazolidine, furan, morpholine, pyridine, pyridazine, pyrazine, oxolan, imidazoline, isoxazolidine, thiophene, 2-isoxazoline, isothiazolidine, 2-isothiazoline, and thiomorpholine,
  7.10 —$(C_3$-$C_7)$-cycloalkyl or
  7.11 =O,
8. —$N(R^{17})_2$, wherein each $R^{17}$ independently is hydrogen atom, phenyl, —$(C_1$-$C_{10})$-alkyl, —C(O)—$(C_1$-$C_7)$-alkyl, —C(O)-phenyl, —C(O)—NH—$(C_1$-$C_7)$-alkyl, —C(O)—O-phenyl, —C(O)—NH-phenyl, —C(O)—$(C_1$-$C_7)$-alkyl, or —$S(O)_y$—$R^{14}$, wherein $R^{14}$ and y are as defined above, and wherein alkyl or phenyl in each case is unsubstituted or mono- to penta-substituted with a substituent or substituents independently selected from the group defined under 1.7.1 to 1.7.11, or the two $R^{17}$ groups, together with the nitrogen atom to which they are bonded, form a heterocycle having 5 to 7 ring atoms,
9. —NH—C(O)—$R^{15}$, wherein $R^{15}$ is
  9.1 a radical selected from the group consisting of pyrrolidine, tetrahydropyridine, piperidine, piperazine, imidazoline, pyrazolidine, furan, morpholine, pyridine, pyridazine, pyrazine, oxolan, imidazoline, isoxazolidine, 2-isoxazoline, isothiazolidine, 2-isothiazoline, thiophene, and thiomorpholine,
    wherein said radical is unsubstituted or mono- to penta-substituted with a substituent or substituents independently selected from the group consisting of substituents defined under 1.7.1 to 1.7.11 above, —$CF_3$, benzyl and —$(C_1$-$C_{10})$-alkyl, wherein alkyl is unsubstituted or mono- to tri-substituted with a substituent or substituents independently selected from the group of substituents defined under 1.7.1 to 1.7.11 above,
  9.2 —$(C_1$-$C_{10})$-alkyl, wherein alkyl is unsubstituted or mono- to penta-substituted with a substituent or substituents independently selected from the group consisting of substituents defined under 1.7.1 to 1.7.11 above, —O—$(C_1$-$C_{10})$-alkyl, wherein alkyl is unsubstituted or mono- to penta-substituted with a substituent or substituents independently selected from the group of substituents defined under 1.7.1 to 1.7.11 above,
  9.3 —$(C_3$-$C_7)$-cycloalkyl,
  9.4 —$N(R^{13})_2$, wherein $R^{13}$ is as defined in 1.7.7 above provided that —$N(R^{13})_2$ is not —$NH_2$, or
  9.5 phenyl, wherein phenyl is unsubstituted or mono- to penta-substituted with a substituent or substituents independently selected from the group consisting of substituents defined under 1.7.1 to 1.7.11 above, —O—$(C_1$-$C_{10})$-alkyl, —CN, —$CF_3$, and —$(C_1$-$C_{10})$-alkyl, wherein alkyl is unsubstituted or mono- to tri-substituted with a substituent or substituents independently selected from the group of substituents defined under 1.7.1 to 1.7.11 above, or two substituents of the phenyl radical form a dioxolane ring,
10. —C(O)—$R^{12}$, wherein $R^{12}$ is phenyl or —$(C_1$-$C_7)$-alkyl, wherein alkyl or phenyl are mono- to penta-substituted with a substituent or substituents independently selected from the group of substituents defined under 1.7.1 to 1.7.11 above,
11. —C(O)—O—$R^{12}$, wherein $R^{12}$ is as defined in 10. above,
12. —O—$(C_1$-$C_6)$-alkyl-O—$(C_1$-$C_6)$-alkyl,
13. —O—$(C_0$-$C_4)$-alkyl-$(C_3$-$C_7)$-cycloalkyl, or
14. —$(C_1$-$C_4)$-alkyl-$N(R^{13})_2$, wherein $R^{13}$ is as defined in 1.7.7 above;

$R^5$ is
1. a hydrogen atom,
2. —$(C_1$-$C_{10})$-alkyl, wherein alkyl is unsubstituted or mono- to penta-substituted with a substituent or substituents independently selected from the group defined under 1.7.1 to 1.7.4 above,
3. —C(O)—$R^9$, wherein $R^9$ is
  —$NH_2$, —$(C_1$-$C_{10})$-alkyl, wherein alkyl is unsubstituted or mono- to penta-substituted with a substituent or substituents independently selected from the group defined under 7.1 to 7.4, or —$N(R^{13})_2$, wherein $R^{13}$ is as defined in 1.7.7 above, or
4. —$S(O)_2$—$R^9$, wherein $R^9$ is as defined in 3. above; or $R^4$ and $R^5$, together with the atom to which they are bonded form a heterocycle; or R³ and R⁵, together with the atom to which they are bonded form a heterocycle containing an additional oxygen atom in the ring; and R⁶, R⁷ and R⁸, independently of one another are hydrogen atom or methyl; or in case b):

the substituents R¹, R² and R⁴ independently of one another are as defined under 1.1 to 1.18 in case a) above;

R³ is
1. —CF₃,
2. —CF₂—CF₃,
3. —CN,
4. —COOH,
5. —NO₂,
6. —NH₂,
7. —O—(C₁-C₁₀)-alkyl, wherein alkyl is unsubstituted or mono- to penta substituted independently of one another by
   7.1 phenyl, which is unsubstituted or mono- to penta-substituted by halogen or —O—(C₁-C₄)-alkyl,
   7.2 halogen,
   7.3 —NH₂,
   7.4 —OH,
   7.5 —COOR¹⁶, wherein R¹⁶ is hydrogen atom or —(C₁-C₁₀)-alkyl,
   7.6 —NO₂,
   7.7 —S(O)_y—R¹⁴, wherein y is zero, 1 or 2, R¹⁴ is —(C₁-C₁₀)-alkyl, phenyl, which is unsubstituted or mono- to penta-substituted with a substituent or substituents independently selected from the group consisting of substituents defined under 1.7.1 to 1.7.11, amino, and —N(R¹³)₂,
      wherein each R¹³ independently is hydrogen atom, phenyl, —(C₁-C₁₀)-alkyl, —C(O)—(C₁-C₇)-alkyl, —C(O)-phenyl, —C(O)—NH—(C₁-C₇)-alkyl, —C(O)—O-phenyl, —C(O)—NH-phenyl, —C(O)—O—(C₁-C₇)-alkyl, or —S(O)_y—R¹⁴, wherein R¹⁴ and y are as defined above, and wherein alkyl or phenyl in each case is unsubstituted or mono- to penta-substituted with a substituent or substituents independently selected from the group defined under 1.7.1 to 1.7.11, or
      the two R¹³ groups, together with the nitrogen atom to which they are bonded, form a heterocycle having 5 to 7 ring atoms,
   7.8 —O-phenyl, wherein phenyl is unsubstituted or mono- to penta-substituted with a substituent or substituents independently selected from the group of substituents defined under 1.7.1 to 1.7.11 above,
   7.9 a radical selected from the group consisting of pyrroline, tetrahydropyridine, piperidine, piperazine, imidazoline, pyrazolidine, furan, morpholine, pyridine, pyridazine, pyrazine, oxolan, imidazoline, isoxazolidine, 2-isoxazoline, isothiazolidine, 2-isothiazoline, thiophene, and thiomorpholine,
   7.10 —(C₃-C₇)-cycloalkyl, or
   7.11 =O,
8. —N(R¹³)₂, wherein R¹³ is as defined in 1.7.7 above,
9. —NH—C(O)—R¹⁵, wherein R¹⁵ is
   9.1 a radical selected from the group consisting of pyrrolidine, tetrahydropyridine, piperidine, piperazine, imidazoline, pyrazolidine, furan, morpholine, pyridine, pyridazine, pyrazine, oxolan, imidazoline, isoxazolidine, 2-isoxazoline, isothiazolidine, 2-isothiazoline, thiophene, and thiomorpholine,
      wherein said radical is unsubstituted or mono- to penta-substituted with a substituent or substituents independently selected from the group consisting of substituents defined under 1.7.1 to 1.7.11 above, —CF₃, benzyl, and —(C₁-C₁₀)-alkyl, wherein alkyl is unsubstituted or mono- to tri-substituted with a substituent or substituents independently selected from the group of substituents defined under 1.7.1 to 1.7.11 above,
   9.2 —(C₁-C₁₀)-alkyl, wherein alkyl is unsubstituted or mono- to penta-substituted with a substituent or substituents independently selected from the group consisting of substituents defined under 1.7.1 to 1.7.11 above, and —O—(C₁-C₁₀)-alkyl, wherein alkyl is unsubstituted or mono- to penta-substituted with a substituent or substituents independently selected from the group of substituents defined under 1.7.1 to 1.7.11 above,
   9.3 —(C₃)-cycloalkyl,
   9.4 —N(R¹³)₂, wherein R¹³ is as defined in 1.7.7 above, or
   9.5 phenyl, wherein phenyl is unsubstituted or mono- to penta-substituted with a substituent or substituents independently selected from the group consisting of substituents defined under 1.7.1 to 1.7.11 above, —O—(C₁-C₁₀)-alkyl, —CN, —CF₃, and —(C₁-C₁₀)-alkyl, wherein alkyl is unsubstituted or mono- to tri-substituted with a substituent or substituents independently selected from the group of substituents defined under 1.7.1 to 1.7.11 above, or two substituents of the phenyl radical form a dioxolane ring,
10. —S(O)_y—R¹⁴, wherein R¹⁴ and y are as defined in 1.7.7 above,
11. —C(O)—R¹², wherein R¹² is phenyl or —(C₁-C₇)-alkyl, wherein alkyl or phenyl are unsubstituted or mono- to penta-substituted with a substituent or substituents independently selected from the group of substituents defined under 1.7.1 to 1.7.11 above,
12. —C(O)—O—R¹², wherein R¹² is as defined in 11. above,
13. —(C₁-C₁₀)-alkyl, wherein alkyl is unsubstituted or mono- to penta-substituted with a substituent or substituents independently selected from the group of substituents defined under 1.7.1 to 1.7.11 above,
14. —O—(C₁-C₆)-alkyl-(C₁-C₆)-alkyl,
15. —O—(C₀-C₄)-alkyl-(C₃-C₇)-cycloalkyl, or
16. —(C₁-C₄)-alkyl-N(R¹³)₂, wherein R¹³ is as defined in 1.7.7 above;

R⁵ is as defined as R⁵ in case a) above; and

R⁶, R⁷ and R⁸ independently of one another are hydrogen atom or methyl.

In a second embodiment, the inhibitor of IκB kinase is a compound of formula (II)

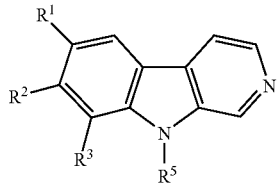

or a stereoisomer or physiologically tolerable salt thereof, wherein:

R¹ and R² are independently of one another hydrogen atom, halogen, cyano, amino, —O—(C₁-C₄)-alkyl, nitro, —CF₃, CF₂—CF₃, —S(O)_y—R¹⁴, or —N(R¹⁸)₂, wherein y is 1 or 2;

R$^{14}$ is amino, —(C$_1$-C$_7$)-alkyl, or phenyl, wherein the alkyl or phenyl is unsubstituted or mono- to tri-substituted with a substituent or substituents independently selected from the group of substituents defined under 1.7.1 to 1.7.11 for the compounds of formula (I);

each R$^{18}$ independently is hydrogen atom, —(C$_1$-C$_7$)-alkyl-C(O)—(C$_1$-C$_7$)-alkyl, —C(O)-phenyl, —C(O)-pyridyl, —C(O)—NH—(C$_1$-C$_4$)-alkyl, —C(O)—O-phenyl, —C(O)—O—(C$_1$-C$_4$)-alkyl or —(C$_1$-C$_{10}$)-alkyl, wherein pyridyl or phenyl in each case is unsubstituted or mono- to tri-substituted with a substituent or substituents independently selected from the group of substituents defined under 1.7.1 to 1.7.11 for the compounds of formula (I), —CF$_3$ benzyl, and —(C$_1$-C$_{10}$)alkyl, and wherein alkyl in each case is unsubstituted or mono- to tri-substituted with a substituent or substituents independently selected from the group of substituents defined under 1.7.1 to 1.7.11 for the compounds of formula (I); or the two R$^{18}$ groups, together with nitrogen atom to which they are bonded, form a heterocycle having 5 to 7 ring atoms;

R$^3$ is cyano, amino, —O—(C$_1$-C$_4$)-alkyl, nitro, —CF$_3$, —CF$_2$—CF$_3$, —S(O)$_y$—R$^{14}$ or —N(R$^{18}$)$_2$, wherein y is 1 or 2;

R$^{14}$ is amino, —(C$_1$-C$_7$)-alkyl, or phenyl, wherein the alkyl or phenyl is unsubstituted or mono- to tri-substituted with a substituent or substituents independently selected from the group of substituents defined under 1.7.1 to 1.7.11 for the compounds of formula (I);

each R$^{18}$ independently is hydrogen atom, —(C$_1$-C$_7$)-alkyl-C(O)—(C$_1$-C$_7$)-alkyl, —C(O)-phenyl, —C(O)-pyridyl, —C(O)—NH—(C$_1$-C$_4$)-alkyl, —C(O)—O-phenyl, —C(O)—O—(C$_1$-C$_4$)-alkyl or —(C$_1$-C$_{10}$)-alkyl, wherein pyridyl or phenyl in each case is unsubstituted or mono- to tri-substituted with a substituent or substituents independently selected from the group of substituents defined under 1.7.1 to 1.7.11 for the compounds of formula (I), —CF$_3$, benzyl, and —(C$_1$-C$_{10}$)alkyl, and wherein alkyl in each case is unsubstituted or mono- to tri-substituted with a substituent or substituents independently selected from the group of substituents defined under 1.7.1 to 1.7.11 for the compounds of formula (I); or the two R$^{18}$ groups, together with nitrogen atom to which they are bonded, form a heterocycle having 5 to 7 ring atoms; and R$^5$ is hydrogen atom, —(C$_1$-C$_{10}$)-alkyl, —C(O)—R$^9$, or —S(O)$_2$—R$^9$, wherein R$^9$ is —(C$_1$-C$_{10}$)-alkyl, —O—(C$_1$-C$_{10}$)-alkyl, or phenyl;

alkyl, in each instance, is unsubstituted or mono- to tri-substituted with a substituent or substituents independently selected from the group of substituents defined under 1.7.1 to 1.7.4 for the compounds of formula (I); and phenyl is unsubstituted or mono- to tri-substituted with a substituent or substituents independently selected from the group of substituents defined under 1.7.1 to 1.7.11 for the compounds of formula (I), and —N(R$^{18}$)$_2$, wherein R$^{18}$ is as defined above.

In a second aspect, the invention provides methods for treating cancer, comprising administering to a patient with cancer an inhibitor of IκB kinase as described for the first aspect of the invention. In some embodiments, the cancer is multiple myeloma.

BRIEF DESCRIPTION OF THE FIGURES

FIG. 5 is an immunoblot showing the effect of compound 1 on phosphorylation of p42/44 MAPK or STAT3. MM.1S cells were pre-treated with compound 1 (10 μM for 90 min) or PS-341 (5 μM for 60 min) and then stimulated by IL-6 (50 ng/mL for 5 min). The cells were harvested, lysed, electrophoresed, and immunoblotted with anti-phospho-STAT3, phospho-p42/44 MAPK, and p42/44 MAPK Abs. These results show that compound 1 does not affect phosphorylation of p42/44 MAPK or STAT3 in MM.1S cells.

FIG. 6 shows the effect of dexamethasone (Dex) on IκBα protein expression and NF-κB activation. (A) MM.1S cells were cultured in the presence of Dex (1 μM for 0-36 h), in the presence or absence of IL-6. The cells were harvested, lysed, electrophoresed, and immunoblotted with anti-phospho-IκBα Abs. (B) MM.1S cells were cultured with either DMSO control or Dex (1 μM for 18 h), stimulated by TNFα (5 ng/mL) or IL-6 (50 ng/mL), and nuclear extracts were subjected to EMSA to assess NF-κB activation. (C) MM.1S cells were pre-treated with either DMSO control or Dex (1 μM for 18 h), and then incubated in the presence of compound 1 (2.5-10 μM for 90 min). The cells were harvested, and nuclear extracts were subjected to EMSA to assess NF-κB activation.

DETAILED DESCRIPTION OF THE INVENTION

Figure 1A:
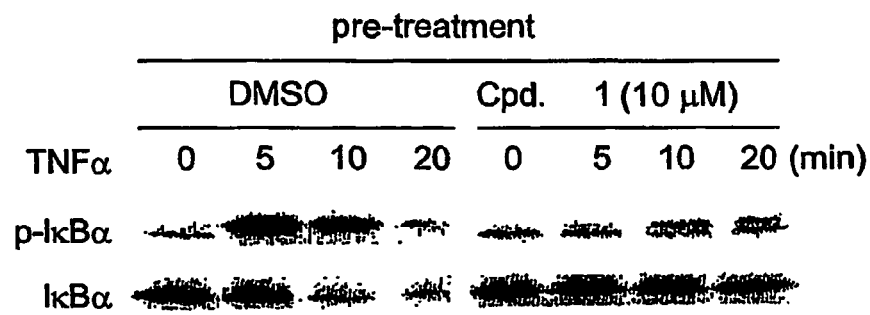
FIG. 1 is an immunoblot showing the effect of compound 1 on phosphorylation and degradation of IκBα. (A) MM.1S cells were pre-treated with compound 1 (10 μM for 90 min), and then stimulated by TNFα (5 ng/mL for 0-20 min). (B) MM.1S cells were pre-treated with 0.125-40 μM compound 1 for 90 min before stimulation by TNFα (5 ng/mL for 5 min). (C) Patient MM cells were pre-treated with compound 1 (10 μM for 90 min), and then stimulated by TNFα (5 ng/mL for 0-10 min). The cells were lysed, electrophoresed, and then immunoblotted with anti-phospho IκBα and anti-IκBα Abs. The results show that compound 1 blocks phosphorylation and degradation of IκBα triggered by TNFα.

The invention relates to methods for inhibiting cancer cell growth. In particular, the invention provides methods for inhibiting cancer cell growth by administering to a cancer cell an inhibitor of IκB kinase as herein described. The invention further provides methods for treating cancer by administering an inhibitor of IκB kinase to a patient with cancer.

The issued patents and published scientific literature referred to herein establishes knowledge that is available to those with skill in the art. All patents, patent applications, and references that are cited herein are hereby incorporated by reference to the same extent as if each was specifically and individually indicated to be incorporated by reference. In the case of inconsistencies, the present disclosure will prevail.

In a first aspect, the invention provides methods for inhibiting cancer cell growth by administering to a cancer cell an inhibitor of IκB kinase (IKK). Preferably, such inhibition is specific, i.e., the IKK inhibitor reduces the ability of IKK to phosphorylate IκBα at a concentration that is lower than the concentration of the inhibitor that is required to produce another, unrelated biological effect. Preferably, the concentration of the inhibitor required for 1 inhibitory activity is at least 2-fold lower, more preferably at least 5-fold lower, even more preferably at least 10-fold lower, and most preferably at least 20-fold lower than the concentration required to produce an unrelated biological effect. The concentration of inhibitor required for IKK inhibitory activity can be determined by any assay suitable for measuring IKK activity, including the assays described in the Examples. The concentration of inhibitor required to produce an unrelated biological effect can be determined by subjecting the inhibitor to a panel of enzymatic, receptor binding, and/or pharmacological assays.

Some preferred IKK inhibitors are beta-carboline compounds, including those described in Rizeler et al., WO 01/68648, the entire teachings of which are hereby incorporated by reference in their entirety, including all compounds, formulae, and synthetic procedures disclosed therein.

In some embodiments, therefore, the method according to this aspect of the invention comprises contacting a cancer cell with an IκB kinase inhibitor of formula (I)

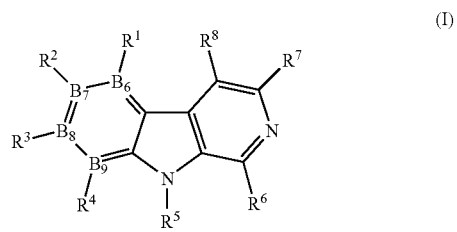

(I)

or a stereoisomer or physiologically tolerable salt thereof, wherein:

$B_6$, $B_7$, $B_8$, and $B_9$ are independently selected from the group consisting of carbon atom and nitrogen atom, where a total of no more than two of $B_6$, $B_7$, $B_8$, and $B_9$ are nitrogen atoms; and in case a):

the substituents $R^1$, $R^2$ and $R^3$ independently of one another are 1.1. hydrogen atom,
1.2. halogen,
1.3. —CN,
1.4. —COOH,
1.5. —NO$_2$,
1.6. —NH$_2$,
1.7. —O—(C$_1$-C$_{10}$)-alkyl, wherein alkyl is unsubstituted or mono- to penta-substituted with a substituent or substituents independently selected from the group consisting of
  1.7.1 phenyl, which is unsubstituted or mono- to penta-substituted by halogen or —O—(C$_1$-C$_4$)-alkyl,
  1.7.2 halogen, 1.7.3 —NH$_2$,
1.7.4 —OH,
1.7.5 —COOR$^{16}$, wherein R$^{16}$ is hydrogen atom or —(C$_1$-C$_{10}$)-alkyl,
1.7.6 —NO$_2$,
1.7.7 —S(O)$_y$—R$^{14}$, wherein y is zero, 1 or 2, and R$^{14}$ is —(C$_1$-C$_{10}$)-alkyl, phenyl, which is unsubstituted or mono- to penta-substituted with a substituent or substituents independently selected from the group defined under 1.7.1 to 1.7.11, amino or —N(R$^{13}$)$_2$, wherein each R$^{13}$ independently is hydrogen atom, phenyl, —(C$_1$-C$_{10}$)-alkyl, —C(O)—(C$_1$-C$_7$)-alkyl, —C(O)-phenyl, —C(O)—NH—(C$_1$-C$_7$)-alkyl, —C(O)—O-phenyl, —C(O)—NH-phenyl, —C(O)—O—(C$_1$-C$_7$)-alkyl, or —S(O)$_y$—R$^{14}$, wherein R$^{14}$ and y are as defined above, and wherein alkyl or phenyl in each case is unsubstituted or mono- to penta-substituted with a substituent or substituents independently selected from the group defined under 1.7.1 to 1.7.11, or
   the two R$^{13}$ groups, together with the nitrogen atom to which they are bonded, form a heterocycle having 5 to 7 ring atoms,
1.7.8 —O-phenyl, wherein phenyl is unsubstituted or mono- to penta-substituted with a substituent or substituents independently selected from the group defined under 1.7.1 to 1.7.11,
1.7.9 a radical selected from the group consisting of pyrrolidine, tetrahydropyridine, piperidine, piperazine, imidazoline, pyrazolidine, furan, morpholine, pyridine, pyridazine, pyrazine, oxolan, imidazoline, isoxazolidine, 2-isoxazoline, isothiazolidine, 2-isothiazoline, thiophene, and thiomorpholine,
1.7.10 —(C$_3$-C$_7$)-cycloalkyl or
1.7.11 =O,
1.8. —N(R$^{13}$)$_2$, wherein R$^{13}$ is as defined in 1.7.7 above,
1.9. —NH—C(O)—R$^{15}$, wherein R$^{15}$ is
   1.9.1 a radical selected from the group consisting of pyrrolidine, tetrahydropyridine, piperidine, piperazine, imidazoline, pyrazolidine, furan, morpholine, pyridine, pyridazine, pyrazine, oxolan, imidazoline, isoxazolidine, 2-isoxazoline, isothiazolidine, 2-isothiazoline, thiophene, and thiomorpholine,
      wherein said radical is unsubstituted or mono- to penta-substituted with a substituent or substituents independently selected from the group consisting of substituents defined under 1.7.1 to 1.7.11 above, —CF$_3$, benzyl, and —(C$_1$-C$_{10}$)-alkyl, wherein alkyl is unsubstituted or mono- to tri-substituted with a substituent or substituents independently selected from the group of substituents defined under 1.7.1 to 1.7.11 above,
   1.9.2 —(C$_1$-C$_{10}$)-alkyl, wherein alkyl is unsubstituted or mono- to penta-substituted with a substituent or substituents independently selected from the group consisting of substituents defined under 1.7.1 to 1.7.11 above and —O—(C$_1$-C$_{10}$)-alkyl, wherein alkyl is unsubstituted or mono- to penta-substituted with a substituent or substituents independently selected from the group of substituents defined under 1.7.1 to 1.7.11 above,
   1.9.3 —(C$_3$-C$_7$)-cycloalkyl,
   1.9.4 —N(R$^{13}$)$_2$, wherein R$^{13}$ is as defined in 1.7.7 above, or
   1.9.5 phenyl, wherein phenyl is unsubstituted or mono- to penta-substituted with a substituent or substituents independently selected from the group consisting of substituents defined under 1.7.1 to 1.7.11 above, —O—(C$_1$-C$_{10}$)-alkyl, CN, —CF$_3$, and —(C$_1$-C$_{10}$)-alkyl, wherein alkyl is unsubstituted or mono- to tri-substituted with a substituent or substituents independently selected from the group of substituents defined under 1.7.1 to 1.7.11 above, or two substituents of the phenyl radical together form a dioxolane ring,
1.10. —S(O)$_y$—R$^{14}$, wherein R$^{14}$ and y are as defined in 1.7.7 above,
1.11. —C(O)—R$^{12}$, wherein R$^{12}$ is phenyl or —(C$_1$-C$_7$)-alkyl, wherein alkyl or phenyl are unsubstituted or mono- to penta-substituted with a substituent or substituents independently selected from the group of substituents defined under 1.7.1 to 1.7.11 above,
1.12. —C(O)—O—R$^{12}$, wherein R$^{12}$ is as defined in 11. above,
1.13. —(C$_1$-C$_{10}$)-alkyl, wherein alkyl is unsubstituted or mono- to penta-substituted with a substituent or substituents independently selected from the group of substituents defined under 1.7.1 to 1.7.11 above,
1.14. —O—(C$_1$-C$_6$)-alkyl-O—(C$_1$-C$_6$)-alkyl,
1.15. —(C$_0$-C$_4$)-alkyl-(C$_3$-C$_7$)-cycloalkyl,
1.16. —(C$_1$-C$_4$)-alkyl-N(R$^{13}$)$_2$, wherein R$^{13}$ is as defined in 1.7.7 above
1.17. —CF$_3$ or
1.18. —CF$_2$—CF$_3$;
R$^4$ is
1. —(C$_1$-C$_{10}$)-alkyl, wherein alkyl is unsubstituted or mono- to penta-substituted with a substituent or substituents independently selected from the group of substituents defined under 1.7.1 to 1.7.11 above,
2. —CF$_3$,
3. —CF$_2$CF$_3$,
4. —CN,
5. —S(O)$_y$—R$^{14}$, wherein R$^{14}$ and y are as defined in 1.7.7 above,
6. —NH$_2$,
7. —O—(C$_1$-C$_{10}$)-alkyl, wherein alkyl is unsubstituted or mono- to penta-substituted independently of one another by
   7.1 phenyl, which is unsubstituted or mono- to penta-substituted by halogen or O—(C$_1$-C$_4$)-alkyl,
   7.2 halogen,
   7.3 —NH$_2$,
   7.4 —OH,
   7.5 —COOR$^{16}$, wherein R$^{16}$ is hydrogen atom or —(C$_1$-C$_{10}$)-alkyl,
   7.6 —NO$_2$,
   7.7 —S(O)$_y$—R$^{14}$, wherein y is zero, 1 or 2, R$^{14}$ is —(C$_1$-C$_{10}$)-alkyl, phenyl, which is unsubstituted or mono- to penta-substituted with a substituent or substituents independently selected from the group of substituents defined under 1.7.1 to 1.7.11 above, amino, and —N(R$^{13}$)$_2$,
      wherein each R$^{13}$ independently is hydrogen atom, phenyl, —(C$_1$-C$_{10}$)-alkyl, —C(O)—(C$_1$-C$_7$)-alkyl, —C(O)-phenyl, —C(O)—NH—(C$_1$-C$_7$)-alkyl, —C(O)—O-phenyl, —C(O)—NH-phenyl, —C(O)—O—(C$_1$-C$_7$)-alkyl, or —S(O)$_y$—R$^{14}$, wherein R$^{14}$ and y are as defined above, and wherein alkyl or phenyl in each case is unsubstituted or mono- to penta-substituted with a substituent or substituents independently selected from the group defined under 1.7.1 to 1.7.11, or
      the two R$^{13}$ groups, together with the nitrogen atom to which they are bonded, form a heterocycle having 5 to 7 ring atoms, 7.8 —O-phenyl, wherein phenyl is unsubstituted or mono- to penta-substituted with a substituent or substituents independently selected from the group of substituents defined under 1.7.1 to 1.7.11 above, 7.9 a radical selected from the group consisting of pyrrolidine, tetrahydropyridine, piperidine, piperazine, imidazoline, pyrazolidine, furan, morpholine, pyridine, pyridazine, pyrazine, oxolan, imidazoline, isoxazolidine, thiophene, 2-isoxazoline, isothiazolidine, 2-isothiazoline, and thiomorpholine, 7.10 —($C_3$-$C_7$)-cycloalkyl or 7.11 =O, 8. —N($R^{17}$)$_2$, wherein each $R^{17}$ independently is hydrogen atom, phenyl, —($C_1$-$C_{10}$)-alkyl, —C(O)—($C_1$-$C_7$)-alkyl, —C(O)-phenyl, —C(O)—NH—($C_1$-$C_7$)-alkyl, —C(O)—O-phenyl, —C(O)—NH-phenyl, —C(O)—O—($C_1$-$C_7$)-alkyl, or —S(O)$_y$—$R^{14}$, wherein $R^{14}$ and y are as defined above, and wherein alkyl or phenyl in each case is unsubstituted or mono- to penta-substituted with a substituent or substituents independently selected from the group defined under 1.7.1 to 1.7.11, or the two $R^{17}$ groups, together with the nitrogen atom to which they are bonded, form a heterocycle having 5 to 7 ring atoms, 9. —NH—C(O)—$R^{15}$, wherein $R^{15}$ is 9.1 a radical selected from the group consisting of pyrrolidine, tetrahydropyridine, piperidine, piperazine, imidazoline, pyrazolidine, furan, morpholine, pyridine, pyridazine, pyrazine, oxolan, imidazoline, isoxazolidine, 2-isoxazoline, isothiazolidine, 2-isothiazoline, thiophene, and thiomorpholine,
wherein said radical is unsubstituted or mono- to penta-substituted with a substituent or substituents independently selected from the group consisting of substituents defined under 1.7.1 to 1.7.11 above, —CF$_3$ benzyl and —($C_1$-$C_{10}$)-alkyl, wherein alkyl is unsubstituted or mono- to tri-substituted with a substituent or substituents independently selected from the group of substituents defined under 1.7.1 to 1.7.11 above, 9.2 —($C_1$-$C_{10}$)-alkyl, wherein alkyl is unsubstituted or mono- to penta-substituted with a substituent or substituents independently selected from the group consisting of substituents defined under 1.7.1 to 1.7.11 above, —O—($C_1$-$C_{10}$)-alkyl, wherein alkyl is unsubstituted or mono- to penta-substituted with a substituent or substituents independently selected from the group of substituents defined under 1.7.1 to 1.7.11 above, 9.3 —($C_3$-$C_7$)-cycloalkyl, 9.4 —N($R^{13}$)$_2$, wherein $R^{13}$ is as defined in 1.7.7 above provided that —N($R^{13}$)$_2$ is not —NH$_2$, or 9.5 phenyl, wherein phenyl is unsubstituted or mono- to penta-substituted with a substituent or substituents independently selected from the group consisting of substituents defined under 1.7.1 to 1.7.11 above, —O—($C_1$-$C_{10}$)-alkyl, —CN, —CF$_3$, and —($C_1$-$C_{10}$)-alkyl, wherein alkyl is unsubstituted or mono- to tri-substituted with a substituent or substituents independently selected from the group of substituents defined under 1.7.1 to 1.7.11 above, or two substituents of the phenyl radical form a dioxolane ring, 10. —C(O)—$R^{12}$, wherein $R^{12}$ is phenyl or —($C_1$-$C_7$)-alkyl, wherein alkyl or phenyl are mono- to penta-substituted with a substituent or substituents independently selected from the group of substituents defined under 1.7.1 to 1.7.11 above, 11. —C(O)—O—$R^{12}$, wherein $R^{12}$ is as defined in 10. above, 12. —O—($C_1$-$C_6$)-alkyl-O—($C_1$-$C_6$)-alkyl, 13. —O—($C_0$-$C_4$)-alkyl-($C_3$-$C_7$)-cycloalkyl, or 14. —($C_1$-$C_4$)-alkyl-N($R^{13}$)$_2$, wherein $R^{13}$ is as defined in 1.7.7 above;

$R^5$ is 1. a hydrogen atom,

2. —($C_1$-$C_{10}$)-alkyl, wherein alkyl is unsubstituted or mono- to penta-substituted with a substituent or substituents independently selected from the group defined under 1.7.1 to 1.7.4 above, 3. —C(O)—$R^9$, wherein $R^9$ is
—NH$_2$, —($C_1$-$C_{10}$)-alkyl, wherein alkyl is unsubstituted or mono- to penta-substituted with a substituent or substituents independently selected from the group defined under 7.1 to 7.4, or —N($R^{13}$)$_2$, wherein $R^{13}$ is as defined in 1.7.7 above, or 4. —S(O)$_2$—$R^9$, wherein $R^9$ is as defined in 3. above; or $R^4$ and $R^5$, together with the atom to which they are bonded form a heterocycle; or $R^3$ and $R^5$, together with the atom to which they are bonded form a heterocycle containing an additional oxygen atom in the ring; and $R^6$, $R^7$ and $R^8$, independently of one another are hydrogen atom or methyl; or in case b):

the substituents $R^1$, $R^2$ and $R^4$ independently of one another are as defined under 1.1 to 1.18 in case a) above;

$R^3$ is

1. —CF$_3$,

2. —CF$_2$—CF$_3$,

3. —CN,

4. —COOH,

5. —NO$_2$,

6. —NH$_2$,

7. —($C_1$-$C_{10}$)-alkyl, wherein alkyl is unsubstituted or mono- to penta substituted independently of one another by 7.1 phenyl, which is unsubstituted or mono- to penta-substituted by halogen or —O—($C_1$-$C_4$)-alkyl, 7.2 halogen, 7.3 —NH$_2$, 7.4 —OH, 7.5 —COOR$^{16}$, wherein $R^{16}$ is hydrogen atom or —($C_1$-$C_{10}$)-alkyl, 7.6 —NO$_2$, 7.7 —S(O)$_y$—$R^{14}$, wherein y is zero, 1 or 2, $R^{14}$ is —($C_1$-$C_{10}$)-alkyl, phenyl, which is unsubstituted or mono- to penta-substituted with a substituent or substituents independently selected from the group consisting of substituents defined under 1.7.1 to 1.7.11, amino, and N($R^{13}$)$_2$,
wherein each $R^{13}$ independently is hydrogen atom, phenyl, —($C_1$-$C_{10}$)-alkyl, —C(O)—($C_1$-$C_7$)-alkyl, —C(O)-phenyl, —C(O)—NH—($C_1$-$C_7$)-alkyl, —C(O)—O-phenyl, —C(O)—NH-phenyl, —C(O)—O—($C_1$-$C_7$)-alkyl, or —S(O)$_y$—$R^{14}$ wherein $R^{14}$ and y are as defined above, and wherein alkyl or phenyl in each case is unsubstituted or mono- to penta-substituted with a substituent or substituents independently selected from the group defined under 1.7.1 to 1.7.11, or
the two $R^{13}$ groups, together with the nitrogen atom to which they are bonded, form a heterocycle having 5 to 7 ring atoms, 7.8 —O-phenyl, wherein phenyl is unsubstituted or mono- to penta-substituted with a substituent or substituents independently selected from the group of substituents defined under 1.7.1 to 1.7.11 above, 7.9 a radical selected from the group consisting of pyrrolidine, tetrahydropyridine, piperidine, piperazine, imidazoline, pyrazolidine, furan, morpholine, pyridine, pyridazine, pyrazine, oxolan, imidazoline, isoxazolidine, 2-isoxazoline, isothiazolidine, 2-isothiazoline, thiophene, and thiomorpholine, 7.10 —$(C_3-C_7)$-cycloalkyl, or 7.11 =O, 8. —$N(R^{13})_2$, wherein $R^{13}$ is as defined in 1.7.7 above, 9. —NH—C(O)—$R^{15}$, wherein $R^{15}$ is 9.1 a radical selected from the group consisting of pyrrolidine, tetrahydropyridine, piperidine, piperazine, imidazoline, pyrazolidine, furan, morpholine, pyridine, pyridazine, pyrazine, oxolan, imidazoline, isoxazolidine, 2-isoxazoline, isothiazolidine, 2-isothiazoline, thiophene, and thiomorpholine,
wherein said radical is unsubstituted or mono- to penta-substituted with a substituent or substituents independently selected from the group consisting of substituents defined under 1.7.1 to 1.7.11 above, —$CF_3$, benzyl, and —$(C_1-C_{10})$-alkyl, wherein alkyl is unsubstituted or mono- to tri-substituted with a substituent or substituents independently selected from the group of substituents defined under 1.7.1 to 1.7.11 above, 9.2 —$(C_1-C_{10})$-alkyl, wherein alkyl is unsubstituted or mono- to penta-substituted with a substituent or substituents independently selected from the group consisting of substituents defined under 1.7.1 to 1.7.11 above, and —O—$(C_1-C_{10})$-alkyl, wherein alkyl is unsubstituted or mono- to penta-substituted with a substituent or substituents independently selected from the group of substituents defined under 1.7.1 to 1.7.11 above, 9.3 —$(C_3-C_7)$-cycloalkyl, 9.4 —$N(R^{13})_2$, wherein $R^{13}$ is as defined in 1.7.7 above, or 9.5 phenyl, wherein phenyl is unsubstituted or mono- to penta-substituted with a substituent or substituents independently selected from the group consisting of substituents defined under 1.7.1 to 1.7.11 above, —O—$(C_1-C_{10})$-alkyl, CN, —$CF_3$, and —$(C_1-C_{10})$-alkyl, wherein alkyl is unsubstituted or mono- to tri-substituted with a substituent or substituents independently selected from the group of substituents defined under 1.7.1 to 1.7.11 above, or two substituents of the phenyl radical form a dioxolane ring, 10. —$S(O)_y$—$R^{14}$ wherein $R^{14}$ and y are as defined in 1.7.7 above, 11. —C(O)—$R^{12}$, wherein $R^{12}$ is phenyl or —$(C_1-C_7)$-alkyl, wherein alkyl or phenyl are unsubstituted or mono- to penta-substituted with a substituent or substituents independently selected from the group of substituents defined under 1.7.1 to 1.7.11 above, 12. —C(O)—O—$R^{12}$, wherein $R^{12}$ is as defined in 11. above, 13. —$(C_1-C_{10})$-alkyl, wherein alkyl is unsubstituted or mono- to penta-substituted with a substituent or substituents independently selected from the group of substituents defined under 1.7.1 to 1.7.11 above, 14. —O—$(C_1-C_6)$-alkyl-O—$(C_1-C_6)$-alkyl, 15. —O—$(C_0-C_4)$-alkyl-$(C_3-C_7)$-cycloalkyl, or 16. —$(C_1-C_4)$-alkyl-$N(R^{13})_2$, wherein $R^{13}$ is as defined in 1.7.7 above;

$R^5$ is as defined as $R^5$ in case a) above; and $R^6$, $R^7$ and $R^8$ independently of one another are hydrogen atom or methyl.

In some embodiments, the IKK inhibitors of formula (I) are compounds of case a), wherein:

$B_6$, $B_7$, $B_8$, and $B_9$ are each a carbon atom; and $R^4$ is —NH—C(O)—$R^{15}$, wherein $R^{15}$ is as defined under 9.1 to 9.5 above.

In some preferred embodiments, $R^{15}$ is:

a radical selected from the group consisting of pyrrolidine, tetrahydropyridine, piperidine, piperazine, imidazoline, pyrazolidine, furan, morpholine, pyridine, pyridazine, pyrazine, oxolan, imidazoline, isoxazolidine, 2-isoxazoline, isothiazolidine, 2-isothiazoline, thiophene, and thiomorpholine,
wherein said radical is unsubstituted or mono- to penta-substituted with a substituent or substituents independently selected from the group consisting of substituents defined under 1.7.1 to 1.7.11 above, —$CF_3$, benzyl, and —$(C_1-C_{10})$-alkyl, wherein alkyl is unsubstituted or mono- to tri-substituted with a substituent or substituents independently selected from the group of substituents defined under 1.7.1 to 1.7.11 above; or phenyl, wherein phenyl is unsubstituted or mono- to penta-substituted with a substituent or substituents independently selected from the group consisting of substituents defined under 1.7.1 to 1.7.11 above, —$(C_1-C_{10})$-alkyl, —CN, —$CF_3$, and —$(C_1-C_{10})$-alkyl, wherein alkyl is unsubstituted or mono- to tri-substituted with a substituent or substituents independently selected from the group of substituents defined under 1.7.1 to 1.7.11 above, or two substituents of the phenyl radical form a dioxolane ring.

In some embodiments, the method according to this aspect of the invention comprises contacting a cancer cell with an IκB kinase inhibitor of formula (II)

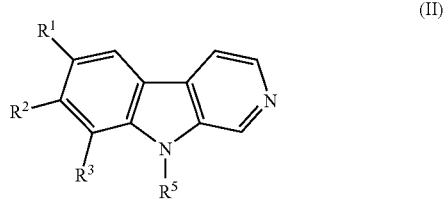

(II)

or a stereoisomer or physiologically tolerable salt thereof, wherein:

$R^1$ and $R^2$ are independently of one another hydrogen atom, halogen, cyano, amino, —O—$(C_1-C_4)$-alkyl, nitro, —$CF_3$—$CF_2$—$CF_3$—$S(O)_y$—$R^{14}$, or —$N(R^{18})_2$, wherein y is 1 or 2;

$R^{14}$ is amino, —$(C_1-C_7)$-alkyl, or phenyl, wherein the alkyl or phenyl is unsubstituted or mono- to tri-substituted with a substituent or substituents independently selected from the group of substituents defined under 1.7.1 to 1.7.11 for the compounds of formula (I);

each $R^{18}$ independently is hydrogen atom, —$(C_1-C_7)$-alkyl-C(O)—$(C_1-C_7)$-alkyl, —C(O)-phenyl, —C(O)-pyridyl, —C(O)—NH—$(C_1-C_4)$-alkyl, —C(O)—O-phenyl, —C(O)—O—$(C_1-C_4)$-alkyl or —($C_1$-$C_{10}$)-alkyl, wherein pyridyl or phenyl in each case is unsubstituted or mono- to tri-substituted with a substituent or substituents independently selected from the group of substituents defined under 1.7.1 to 1.7.11 for the compounds of formula (I), —$CF_3$, benzyl, and —($C_1$-$C_{10}$)alkyl, and wherein alkyl in each case is unsubstituted or mono- to tri-substituted with a substituent or substituents independently selected from the group of substituents defined under 1.7.1 to 1.7.11 for the compounds of formula (I); or the two $R^{18}$ groups, together with nitrogen atom to which they are bonded, form a heterocycle having 5 to 7 ring atoms;

$R^3$ is cyano, amino, —O—($C_1$-$C_4$)-alkyl, nitro, —$CF_3$, —$CF_2$—$CF_3$, —S(O)$_y$—$R^{14}$, or —N($R^{18}$)$_2$, wherein y is 1 or 2;

$R^{14}$ is amino, —($C_1$-$C_7$)-alkyl, or phenyl, wherein the alkyl or phenyl is unsubstituted or mono- to tri-substituted with a substituent or substituents independently selected from the group of substituents defined under 1.7.1 to 1.7.11 for the compounds of formula (I);

each $R^{18}$ independently is hydrogen atom, —($C_1$-$C_7$)-alkyl-C(O)—($C_1$-$C_7$)-alkyl, —C(O)-phenyl, —C(O)-pyridyl, —C(O)—NH—($C_1$-$C_4$)-alkyl, —C(O)—O-phenyl, —C(O)$_4$— ($C_1$-$C_4$)-alkyl or —($C_1$-$C_{10}$)-alkyl, wherein pyridyl or phenyl in each case is unsubstituted or mono- to tri-substituted with a substituent or substituents independently selected from the group of substituents defined under 1.7.1 to 1.7.11 for the compounds of formula (I), —$CF_3$, benzyl, and —($C_1$-$C_{10}$)alkyl, and wherein alkyl in each case is unsubstituted or mono- to tri-substituted with a substituent or substituents independently selected from the group of substituents defined under 1.7.1 to 1.7.11 for the compounds of formula (I); or the two $R^{18}$ groups, together with nitrogen atom to which they are bonded, form a heterocycle having 5 to 7 ring atoms; and $R^5$ is hydrogen atom, —($C_1$-$C_{10}$)-alkyl, —C(O)—$R^9$, or —S(O)$_2$—$R^9$, wherein $R^9$ is —($C_1$-$C_{10}$)-alkyl, —O—($C_1$-$C_{10}$)-alkyl, or phenyl;

alkyl, in each instance, is unsubstituted or mono- to tri-substituted with a substituent or substituents independently selected from the group of substituents defined under 1.7.1 to 1.7.4 for the compounds of formula (I); and phenyl is unsubstituted or mono- to tri-substituted with a substituent or substituents independently selected from the group of substituents defined under 1.7.1 to 1.7.11 for the compounds of formula (I), and —N($R^{18}$)$_2$, wherein $R^{18}$ is as defined above.

In some embodiments, the IKK inhibitor is a compound of formula (II) as described above, wherein:

$R^1$ is bromo, —$CF_3$ or chloro;

$R^2$ is hydrogen atom or O—($C_1$-$C_2$)-alkyl;

$R^3$ is —N($R^{18}$)$_2$, wherein each $R^{18}$ independently is hydrogen atom, —N—C(O)-pyridyl, —C(O)-phenyl, —($C_1$-$C_7$)-alkyl, —C(O)—($C_1$-$C_4$)-alkyl or (O)—O—($C_1$-$C_4$)-alkyl, wherein alkyl or phenyl, in each instance, is unsubstituted or mono- to tri-substituted with a substituent or substituents independently selected from the group consisting of halogen and —O—($C_1$-$C_2$)-alkyl; and $R^5$ is hydrogen atom, methyl or —S(O)$_2$—$CH_3$.

In various other embodiments, the IKK inhibitor is a compound of formula (II), wherein:

$R^1$ is chloro, $R^3$ is —H—C(O)—$CH_2$—O—$CH_3$, and $R^2$ and $R^5$ are each hydrogen atom; or $R^1$ is chloro, $R^3$ is —N—C(O)-pyridyl, wherein pyridyl is unsubstituted or substituted by chloro, $R^2$ is hydrogen atom or —O—$CH_3$, and $R^5$ is hydrogen atom; or $R^1$ is chloro, $R^3$ is —N—C(O)-phenyl, wherein phenyl is mono- or di-substituted by fluoro, and $R^2$ and $R^5$ are each hydrogen atom.

In some particularly preferred embodiments, the IKK inhibitor is selected from the group consisting of N-(6-Chloro-9H-carbolin-8-yl)-nicotinamide, including the bismesylate salt, bistrifluoracetate salt and bishydrochloride salt thereof, N-(6-Chloro-9H-carbolin-8-yl)-3,4-difluoro-benzamide, including the hydrochloride salt thereof, N-(6-Chloro-7-methoxy-9H-carbolin-8-yl)-nicotinamide, including the bistrifluoracetate salt and bishydrochloride salt thereof, and 6-Chloro-N-(6-chloro-9H-carbolin-8-yl)-nicotinamide.

In one particularly preferred embodiment, the method according to this aspect of the invention comprises contacting a cancer cell with N-(6-chloro-9H-β-carbolin-8-yl)nicotinamide or a stereoisomer or physiologically tolerable salt thereof.

The IκB kinase inhibitors of formula (I) or formula (II) preferably are synthesized as described in Rizeler et al., WO 01/68648. The preparation of physiologically tolerable salts of compounds of formula (I) or formula (II) capable of salt formation, including their stereoisomeric forms, can be carried out according to methods known in the art. With basic reagents such as hydroxides, carbonates, hydrogencarbonates, alkoxides and also ammonia or organic bases, for example trimethyl- or triethylamine, ethanolamine or triethanolamine or alternatively basic amino acids, for example lysine, ornithine or arginine, the carboxylic adds form stable alkali metal, alkaline earth metal or optionally substituted ammonium salts. If the compounds of the formula I contain basic groups, stable acid addition salts can also be prepared using strong acids. For this, both inorganic and organic acids such as hydrochloric, hydrobromic, sulfuric, phosphoric, methanesulfonic, benzenesulfonic, p-toluenesulfonic, 4-bromobenzenesulfonic, cyclohexylamidosulfonic, trifluoromethylsulfonic, acetic, oxalic, tartaric, succinic or trifluoroacetic acid are suitable.

The term "alkyl" by itself or as part on another substituent, unless otherwise stated means a straight or branched chain hydrocarbon radical having 1 to 10 carbon atoms such as methyl, ethyl, n-propyl, isopropyl, n-butyl, tertiary-butyl, pentyl, hexyl, heptyl, nonyl, octyl, decanyl or cycloalkyl having 3 to 7 carbon atoms such as cylopropyl, cyclobutyl, cyclohexyl or cycloheptyl.

The term "alkoxy" by itself or as part on another substituent, unless otherwise stated means —O-alkyl or —O-substituted alkyl.

The term "heterocycle having 5 to 7 ring atoms" refers to a radical of a monocyclic saturated system having 5 to 7 ring members, which contains 1, 2 or 3 heteroatoms as ring members. Examples of heteroatoms are N, O and S. Examples of such heterocycles having 5 to 7 ring atoms include, without limitation, pyrrolidine, tetrahydropyridine, piperidine, piperazine, imidazoline, pyrazolidine, furan, morpholine, pyridine, pyridazine, pyrazine, oxolan, imidazoline, isoxazolidine, 2-isoxazoline, isothiazolidine, 2-isothiazoline, thiophene and thiomorpholine.

Unless otherwise stated, the term "aryl", whether by itself or as part of another substituent, refers to an organic radical derived from an aromatic molecule by removal of one atom;

nonlimiting examples of such aryl groups include phenyl, pyridyl, thiazolyl, morpholinyl and naphthyl.

The term "substituted alkyl" means an alkyl radical substituted at one or more positions by one or more radicals of the group halogen, nitro, sulfo, amino, substituted amino, carboxyl, alkoxy, —O-aryl, —O-substituted aryl, and hydroxyl.

The term "substituted aryl" means an aryl radical substituted at one or more positions by one or more radicals of the group halogen, alkyl, substituted alkyl, nitro, sulfo, amino, alkoxy, aryl, substituted aryl, or hydroxyl groups, preferred is an aryl radical substituted at 1 to 3 positions by 1 to 3 groups.

The term "substituted amino" refers to —N(R$^{13}$)$_2$ wherein R$^{13}$ at each occurrence is independently selected from the group consisting of hydrogen atom, sulfo, alkyl, aryl, —C(O)-alkyl, C(O)—NH-aryl, —C(O)—O-aryl, —C(O)—O-alkyl, or C(O)—O-aryl, wherein each alkyl or aryl may be independently substituted.

The term "sulfo" refers to —S(O)$_y$—R$^{14}$, wherein R$^{14}$ is an alkyl, aryl, substituted aryl, substituted alkyl, amino, or substituted amino and y is zero, one or two.

The term "halogen" is understood as meaning fluorine, chlorine, bromine or iodine.

The term "—(C$_1$-C$_n$)-alkyl" is understood as meaning a hydrocarbon radical, the carbon chain of which is linear or branched and contains 1 to n carbon atoms.

For purposes of the invention, the term "cancer cell" refers to any cell that proliferates abnormally, including, without limitation, pancreatic, colon, breast, prostate, renal, lung, ovarian, gastric, esophageal, hepatocellular, or head and neck cancer cells, melanoma cells, leukemia cells, and multiple myeloma cells. In some embodiments, the cancer cell is grown in cell culture, including primary cultures and immortalized cell lines. In some other embodiments, the cancer cell is in an animal, preferably a mammal. As used herein, the term "mammal" includes, without limitation rats, mice, dogs, pigs, rabbits, non-human primates, and humans.

In a second aspect, the invention provides methods for treating cancer, comprising administering to a patient with cancer an inhibitor of IκB kinase. Preferred inhibitors of IκB kinase for use in this aspect of the invention are those described for use in the first aspect of the invention.

As used herein, the term "cancer" is used to mean a condition in which a cell in a patient's body undergoes abnormal, uncontrolled proliferation. The abnormal cell may proliferate to form a solid tumor, or may proliferate to form a multitude of cells (e.g., leukemia). Preferably, the cancer of the invention is metastatic. Because cancer is defined to be the abnormal, uncontrolled proliferation of a cell, the term does not encompass the normal proliferation of a cell, such as a stem cell or a spermatocyte.

In some embodiments, the cancer patient has a hematologic malignancy. Non-limiting examples of hematologic malignancy include acute myeloid leukemia (AML), chronic myelogenous leukemia (CML), acute lymphoblastic leukemia (ALL), chronic lymphocytic leukemia (CLL), Hodgkin's disease (HD), non-Hodgkin's lymphoma (NHL), multiple myeloma (MM), macroglobulinemia (Waldstrom's), myelodysplastic syndromes (MDS), including refractory anemia with excess blasts (RAEB) and RAEB in transformation (RAEB-T), and myeloproliferative syndromes. In some other embodiments, the cancer patient suffers from pancreatic, colon, breast, prostate (including androgen-dependent and androgen-independent prostate cancer), renal, lung, ovarian, gastric, esophageal, hepatocellular, or head and neck cancer or melanoma. In some other embodiments, the cancer patient suffers from a brain tumor, bone tumor, or soft tissue sarcoma.

The IκB kinase inhibitor can be administered by any pharmaceutically acceptable route, including, without limitation, parenteral (including intravenous, subcutaneous, and intramuscular), oral, sublingual, transdermal, topical, intranasal, intratracheal, intrarectal, intraocular, and vaginal. For the treatment of an adult patient weighing approximately 70 kg, depending on the efficacy of the compound according to formula (I) or formula (II), daily doses of approximately 20 mg to 1000 mg of active compound, preferably from approximately 100 mg to 500 mg, are indicated. Under certain circumstances, however, even higher or lower daily doses may be appropriate. The administration of the daily dose can be carried out both by single administration in the form of an individual dose unit or else of a number of smaller dose units and by multiple administration of subdivided doses at specific intervals.

Both monotherapy and combination therapy regimens are contemplated within the scope of this invention. For purposes of the invention, the term "monotherapy" refers to treatment with an IκB kinase inhibitor, without concurrent treatment with another antitumor agent. For purposes of the invention, the term "combination therapy" refers to concurrent therapy with an IκB kinase inhibitor and another antitumor agent. The term "concurrent" is intended to encompass simultaneous, sequential, and alternating treatments.

In some embodiments, the antitumor agent is selected from the group consisting of cytotoxic chemotherapy, radiotherapy or immunotherapy. Non-limiting examples of cytotoxic agents suitable for use in combination with IκB kinase inhibitors include gemcitabine, irinotecan, 5-fluorouricil, taxanes such as taxol or taxotere, platinum agents such as cisplatin or carboplatin, anthracyclins such as doxorubicin, mitoxantrone, and Doxil™, alkylating agents such as melphalan and cyclophosphamide, fludarabine, and dexamethasone.

In some other embodiments, the IκB kinase inhibitor is administered with another agent that inhibits the activity of NF-κB, including, without limitation, proteasome inhibitors. Examples of proteasome inhibitors suitable for use in combination with an IκB kinase inhibitor include, but are not limited to, those disclosed in Adams et al., U.S. Pat. No. 5,780,454 (1998), U.S. Pat. No. 6,066,730 (2000), and U.S. Pat. No. 6,083,903 (2000). One such proteasome inhibitor is N-pyrazinecarbonyl-L-phenylalanine-L-leucineboronic acid.

The examples below are intended to further illustrate certain preferred embodiments of the invention, and are not intended to limit the scope of the invention.

EXAMPLES

Example 1

Materials and Methods

MM Derived Cell Lines and Patient MM Cells

Dex-sensitive (MM.1S) human MM cell line was kindly provided by Dr. Steven Rosen (Northwestern University, Chicago, Ill.). RPMI8226 and U266 human MM cells were obtained from American Type Culture Collection (Rockville, Md.). All MM cell lines cultured in RPMI-1640 containing 10% fetal bovine serum (FBS, Sigma Chemical Co., St. Louis, Mo.), 2 μM L-glutamine, 100 U/mL penicillin (Pen) and 100 μg/mL streptomycin (Strep) (GIBCO, Grand Island, N.Y.). Patient MM cells were purified from patient BM aspirates using RosetteSep separation system (StemCell Technologies, Vancouver, Canada). The purity of MM cells was confirmed by flow cytometry using PE-conjugated anti-CD138 antibody (Beckton Dickinson Co.).

BMSC Cultures

BM specimens were obtained from patients with MM. Mononuclear cells (MNCs) separated by Ficoll-Hipaque density sedimentation were used to established long-term BM cultures, as previously described (Uchiyama et al., *Blood* 82:3712-3720 (1993)). When an adherent cell monolayer had developed, cells were harvested in Hank's Buffered Saline Solution (HBSS) containing 0.25% trypsin and 0.02% EDTA, washed, and collected by centrifugation.

Inhibitors

The proteasome inhibitor PS-341 and the IκBα kinase (IKK) inhibitor compound 1 (Millennium Pharmaceuticals, Cambridge, Mass.) were dissolved in DMSO and stored at −20° C. until use. PS-341 and compound 1 were diluted in culture medium immediately before use, and PS-341 and compound 1 control media contained <0.1% DMSO. MAPK kinase (MEK) inhibitor PD98059 was purchased from Cell Signaling (Beverly, Mass.).

DNA Synthesis

Proliferation was measured as previously described (Hideshima et al., *Blood* 96:2943 (2000)). MM cells (3×10$^4$ cells/well) were incubated in 96-well culture plates (Costar, Cambridge, Mass.) in the presence of media, PS-341, compound 1 and/or Dex or recombinant human IL-6 (Genetics Institute, Cambridge, Mass.) for 48 h at 37° C. DNA synthesis was measured by [$^3$H]-thymidine ([$^3$H]-TdR, NEN Products, Boston, Mass.) uptake. Cells were pulsed with [$^3$H]TdR (0.5 μCi/well) during the last 8 h of 48 h cultures. All experiments were performed in triplicate.

Growth Inhibition Assay

The inhibitory effect of PS-341 and compound 1 on MM growth was assessed by measuring 3-(4,5-dimethylthiazol-2-yl)-2,5-diphenyl tetrasodium bromide (MTT) dye absorbance of the cells. Cells from 48 h cultures were pulsed with 10 mL of 5 mg/mL MTT to each well for the last 4 h of 48 h cultures, followed by 100 μL isopropanol containing 0.04N HCl. Absorbance was measured at 570 nm using a spectrophotometer (Molecular Devices Corp., Sunnyvale Calif.).

Immunoblotting

MM cells were cultured with PS-341 or compound 1; harvested; washed; and lysed using lysis buffer: 50 mM Tris-HCl (pH 7.4), 150 mM NaCl, 1% NP-40, 5 mM EDTA, 5 mM NaF, 2 mM Na$_3$VO$_4$, 1 mM PMSF, 5 μg/mL leupeptin, and 5 μg/mL aprotinin. For detection of phospho-IκBα, IκBα, phospho-MAPK, phospho-STAT3, ERK2 or alpha-tubulin, cell lysates were subjected SDS-PAGE, transferred to PVDF membrane (Bio-Rad Laboratories, Hercules, Calif.), and immunoblotted with anti-phospho-IκBα, -IκBα, -phospho-MAPK, or -phospho-STAT3 Abs (Cell Signaling, Beverly, Mass.), and anti-alpha-tubulin (Sigma) Abs.

Electrophoretic Mobility Shift Analysis

Electrophoretic mobility shift analyses (EMSA) were carried out as in previous studies (Hideshima et al., *Oncogene* 20:4519 (2001); Hideshima et al., *Cancer Res.* 61:3071 (2001)). Briefly, MM.1S cells were pre-incubated with PS-341 (5 μM for 1 h) and compound 1 (10 μM for 90 min) before stimulation with TNFα (5 ng/mL) for 10 or 20 min. Cells were then pelleted, resuspended in 400 μL of hypotonic lysis buffer (20 mM HEPES, pH 7.9, 10 mM KCl, 1 mM EDTA, 0.2% Triton X-100, 1 mM Na$_3$VO$_4$, 5 mM NaF, 1 mM PMSF, 5 μg/mL leupeptin, 5 μg/mL aprotinin), and kept on ice for 20 min. After centrifugation (14000 g for 5 min) at 4° C., the nuclear pellet was extracted with 100 μL hypertonic lysis buffer (20 mM HEPES, pH 7.9, 400 mM NaCl, 1 mM EDTA, 1 mM Na$_3$VO$_4$, 5 mM NaF, 1 mM PMSF, 5 μg/mL leupeptin, 5 μg/mL aprotinin) on ice for 20 min. After centrifugation (14000 g for 5 min) at 4° C., the supernatant was collected as nuclear extract. Double-stranded NF-κB consensus oligonucleotide probe (5'-GGGGACTTTCCC-3', Santa Cruz Biotech.) was end-labeled with [($^{32}$P)ATP (50 μCi at 222 TBq/mM; NEN, Boston, Mass.). Binding reactions containing 1 ng of oligonucleotide and 5 μg of nuclear protein were conducted at room temperature for 20 min in a total volume of 10 μL of binding buffer (10 mM Tris-HCl, pH 7.5, 50 mM NaCl, 1 mM MgCl$_2$, 0.5 mM EDTA, 0.5 mM DTT, 4% glycerol (v/v), and 0.5 μg poly (dI-dC) (Pharmada, Peapack, N.J.). For supershift analysis, 1 μg of anti-p65 NF-κB Ab was added 5 min before the reaction mixtures, immediately after addition of radiolabeled probe. The samples were loaded onto a 4% polyacrylamide gel, transferred to Whatman paper (Whatman International, Maidstone, U.K.), and visualized by autoradiography.

Flow Cytometric Analysis

For cell cycle analysis, MM cells cultured for 24-48 h in compound 1 (10 μM), Dex (1 μM); IL-6 (20 ng/mL), or control media were harvested, washed with phosphate-buffered saline (PBS), fixed with 70% ethanol, and treated with 10 μg/mL of RNase (Roche Diagnostics Corp., Indianapolis, Ind.). Cells were then stained with propidium iodine (PI, Sigma) (5 μg/mL). For detection of ICAM-1 expression, MM cells cultured in TNFα (5 ng/mL) in the presence or absence of compound 1 (10 μM) were harvested, washed with PBS, and stained with mouse IgG isotype control or FITC-conjugated mouse anti-human CD54 Ab. Both cell cycle profile and ICAM-1 expression were determined using an Epics (Coulter Immunology, Hialeah, Fla.) flow cytometer, as in prior studies (Hideshima et al., *Oncogene* 20:4519 (2001)).

Effect of Compound 1 on Paracrine MM Cell Growth in the BM

To evaluate growth stimulation and signaling in MM cells adherent to BMSCs, 3×10$^4$ MM.1S cells were cultured in BMSC coated 96-well plates for 48 h, in the presence or absence of compound 1. DNA synthesis was measured as described above. The Duoset ELISA (R&D System) was used to measure IL-6 in supernatants of 48 h cultures of BMSCs with or without MM.1S cells, in the presence or absence of compound 1.

Statistical Analysis

Statistical significance of differences observed in drug-treated versus control cultures was determined using the Student's t-test. The minimal level of significance was P<0.05.

Example 2

Synthesis of N-(6-chloro-9H-β-carbolin-8-yl)-nicotinamide (compound 1)

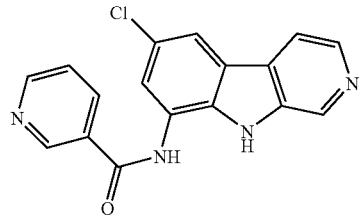 [SMILES: O=C(Nc1cc(Cl)cc2c1[nH]c1cnccc12)c1cccnc1]

To a solution of norharman (2.0 g, 11.9 mmol) in water (89 mL) and 1M aqueous HCl (29.8 mL, 29.8 mmol) was added N-chlorosuccinimide (3.17 g, 23.8 mmol) portionwise. The resulting solution was stirred at RT for 6 h, and then at 0° C. to 5° C. for 12 h. The reaction was diluted with water (100 mL) and basified cautiously with solid $K_2CO_3$ (4.3 g). After stirring at RT for 1 h, the product was collected and washed with water. The crude product was refluxed in chloroform for 1 h and filtered after cooling to 15° C. to provide 2.05 g of 7-chloro-carboline.

A mixture 7-chloro-β-carboline (500 mg, 2.48 mmol) in concentrated nitric acid (20 mL) was stirred at RT for 22 h. The reaction mixture was carefully poured into cold (3° C. to 5° C.) water (50 mL), and after stirring for 2 h the precipitate was collected. The solid was suspended in saturated aqueous $NaHCO_3$ (50 mL) and stirred at RT for 12 h. The product was filtered and washed with water to provide 550 mg of 7-chloro-9-nitro-β-carboline.

To a suspension of 7-chloro-9-nitro-β-carboline (548 mg, 2.22 mmol) in EtOH (14 mL) at 65° C. to 70° C. was added tin chloride dihydrate (2.5 g, 11.1 mmol). Thereafter, 6M aqueous HCl (14 mL) was added dropwise. The mixture was stirred at 70° C. to 80° C. for 3.5 h and then partitioned slowly into saturated aqueous $NaHCO_3$ (150 mL) and EtOAc (100 mL). The aqueous phase was extracted (2 times) and the combined organic solutions dried (brine; $NaSO_4$) and concentrated to give 484 mg of 9-amino-7-chloro-β-carboline.

To a cold (3-5° C.) solution of 9-amino-7-chloro-β-carboline (2.75 g, 12.7 mmol) in pyridine (150 mL) was added nicotinyl chloride hydrochloride (2.82 g, 15.8 mmol). The reaction was allowed to warm to RT and stirred for 20 h before diluting the reaction with water (100 mL) and 1M NaOH (25 mL). After stirring for 1 h at RT, the mixture was poured into water (200 mL). The mixture was allowed to stand for 1 h and the product was filtered to provide 3.80 g of the title compound after washing with water and drying under reduced pressure at RT.

Example 3

Compound 1 Inhibits IκB Kinase Activity

Isolation of the IκB Kinase Complex

The IκB kinase complex was prepared by fist diluting 10 mL of HeLa S3 cell-extracts S100 fraction with 40 mL of 50 mM HEPES pH 7.5. Then, 40% ammonium sulfate was added and incubated on ice for 30 minutes. Precipitated pellet was redissolved with 5 mL of SEC buffer (50 mM HEPES pH 7.5, 1 mM DTT, 0.5 mM EDTA, 10 mM 2-glycerphosphate), clarified by centrifugation at 20,000×g for 15 min, and filtered through a 0.22 μm filter unit. Sample was loaded onto a 320-mL Superose-6 FPLC column (Amersham Pharmacia Biotech AB, Uppsala, Sweden) equilibrated with SEC buffer operated at 2 mL/min flow rate at 4° C. Fractions spanning the 670-kDa molecular weight marker were pooled for activation.

Activation of the IκB Kinase Complex

The kinase-containing pool was activated by incubation with 100 nM MEKK1Δ, 250 μM MgATP, 10 mM $MgCl_2$, 5 mM DTT, 10 mM 2-glycerophosphate, and 2.5 μM Microcystin-LR for 45 min at 37° C. Activated enzyme was stored at −80° C. until further use.

Assay of IκB Kinase Activity

Per well of a 96-well plate, compounds at various concentrations in 2 μL DMSO were pre-incubated for 30 min at 25° C. with 43 μL of activated enzyme diluted [1:25] with assay buffer (50 mM HEPES pH 7.5, 5 mM DTT, 10 mM $MgCl_2$, 10 mM 2-glycerophosphate, 2.5 μM Microcystin-LR). Five microliters of peptide substrate (biotin-$(CH_2)_6$-DRHDS-GLDSMKD-$CONH_2$) at 200 μM stock solution was added to each well and incubated for 1 hour before quenching with 150 μL of 50 mM HEPES pH 7.5, 0.1% BSA, 50 mM EDTA plus [1:200] antibody. Quenched kinase reaction samples and phospho-peptide-calibration standards (biotin-$(CH_2)_6$-DRHDS[PO3]GLDSMKD-$CONH_2$, serially diluted in assay buffer) at 100 μL per well were transferred to a Protein-A plate (Pierce Chemical Co., Rockford, Ill., USA) and incubated for 2 hours with shaking. Following 3 washes with PBS, 100 μL of 0.5 μg/mL streptavidin conjugated with horseradish peroxidase (UP) diluted with 50 mM HEPES/0.1% BSA, was added for 30 minutes. After 5 washes with PBS, 100 μL TMB substrate (Kirkegaard & Perry Laboratories, Gaithersburg, Md., USA) was added and color development was stopped by adding 100 μL of 0.18 M $H_2SO_4$. Absorbance signals were recorded at 450 nm. Calibration-curve standards were fitted by linear regression using a 4-parameter dose-response equation. Based on this standard curve, levels of kinase activity were calculated in order to determine inhibition activity of candidate pharmacological agents. The inhibitor compound 1 exhibits an $IC_{50}$ of 0.052 μM in this assay.

Example 4

Compound 1 Inhibits IκBα Phosphorylation in MM.1S Cells and Patient MM Cells

Figure 1B:
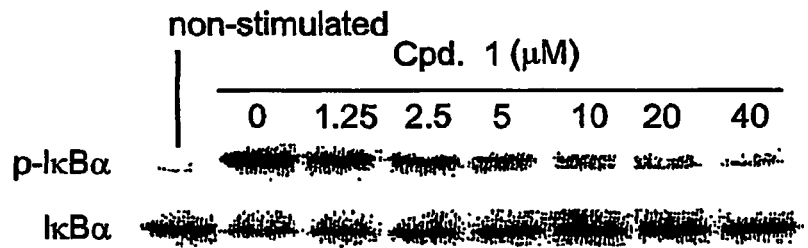
Figure 1C:
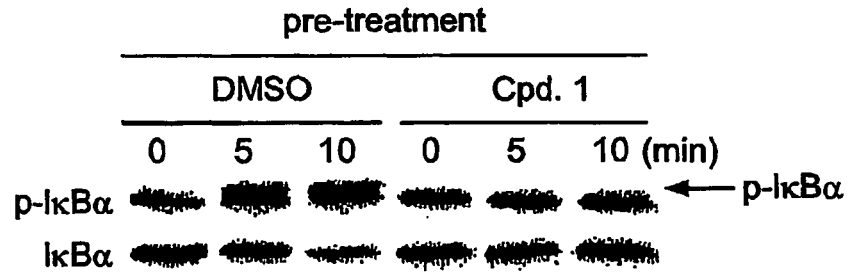

Inhibition of IκBα phosphorylation by compound 1 was assayed in MM.1S and patient MM cells triggered by TNFα. As seen in FIG. 1A, serine phosphorylation and degradation of IκBα were significantly induced after 5 and 10 min TNFα treatment of cells in DMSO control media, whereas phosphorylation and degradation of IκBα were completely blocked by compound 1 pre-treatment of MM.1S cells. To study the dose-dependent effect of compound 1, MM.1S cells were pre-treated with 1.25-40 μM compound 1 for 90 min, and then stimulated by TNFα (5 ng/mL). As can be seen in FIG. 1B, phosphorylation of IκBα was completely inhibited by ≥5 μM compound 1. As in MM.1S cells, compound 1 also inhibited phosphorylation and degradation of IκBα triggered by TNFα in patient MM cells (FIG. 1C). These results demonstrate a time and a dose dependent inhibitory effect of compound 1 on phosphorylation and degradation of IκBα.

Example 5

Compound 1 Inhibits NF-κB Activation in MM.1S Cells

Figure 2:
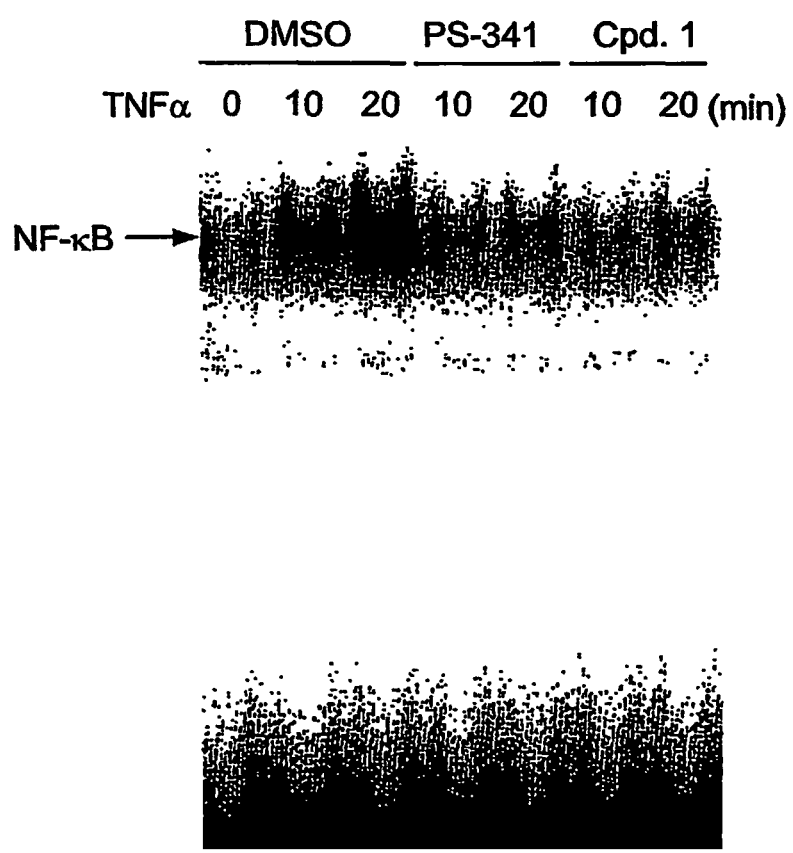
FIG. 2 shows the results of electrophoretic mobility shift assay (EMSA) analysis of the effect of compound 1 on NF-κB activation. MM.1S cells were pre-treated with compound 1 (10 μM for 90 min), and then stimulated by TNFα (5 ng/mL for 0-20 min). Nuclear extracts of the cells were subjected to EMSA. PS-341 served as a positive control for the inhibition of NF-κB activation, as described in Hideshima et al., *Cancer Res.* 61:3071 (2001). These results show that compound 1 blocks NF-κB activation triggered by TNFα.

Since NF-κB activation requires phosphorylation, ubiquitination, and degradation of IκBα, we next examined whether compound 1 could inhibit NF-κB activation, assessed by EMSA. MM.1S cells pre-treated with either DMSO control media or compound 1 (10 μM for 90 min) were stimulated by TNFα (5 ng/mL for 0-20 min). As can be seen in FIG. 2, NF-κB activation was completely inhibited by compound 1 pre-treatment. PS-341 served as positive control for inhibition of NF-κB activation, as previously reported (Hideshima et al., *Oncogene* 20:4519 (2001); Hideshima et al., *Cancer Res.* 61:3071 (2001)).

Example 6

Compound 1 Decreases Viability of MM Cell Lines

Figure 3A:
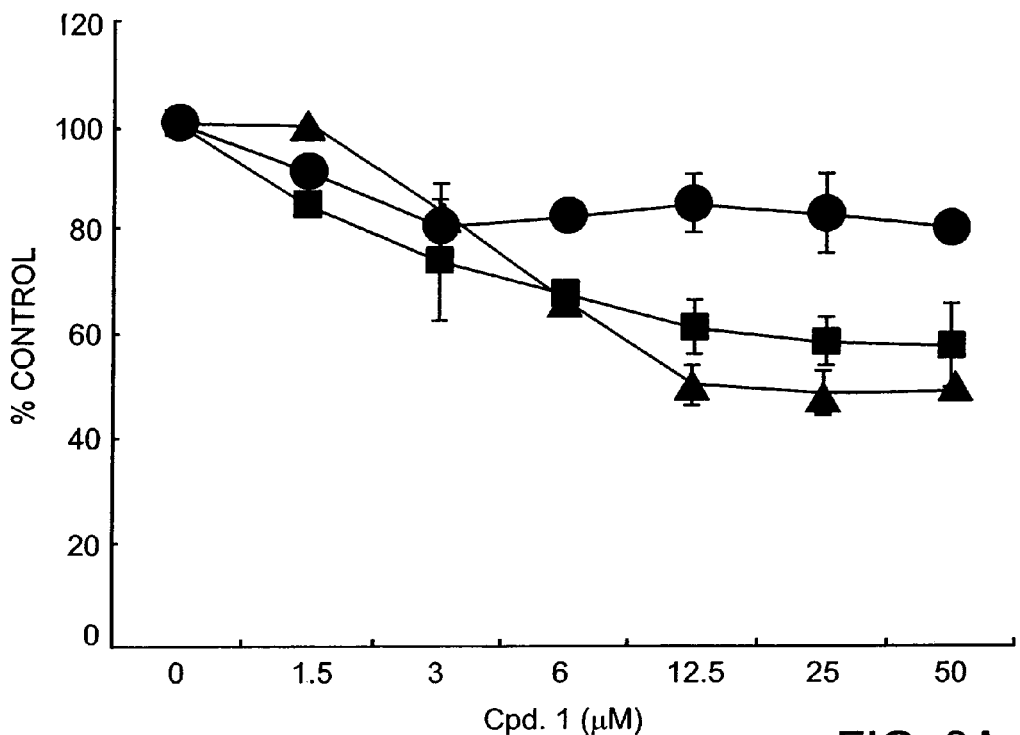
FIG. 3 is a graphical representation of an assay to determine the effect of compound 1 (A) and PS-341 (B) on DNA synthesis in multiple myeloma (MM) cell lines. MM.1S (●), U266 (▲), and RPMI8226 (■) cells were cultured in the presence of compound 1 (1.5-5.0 μM) or PS-341 (0.00001-10 μM for 48 h. DNA synthesis was assessed by [$^3$H]-TdR uptake.
Figure 3B:
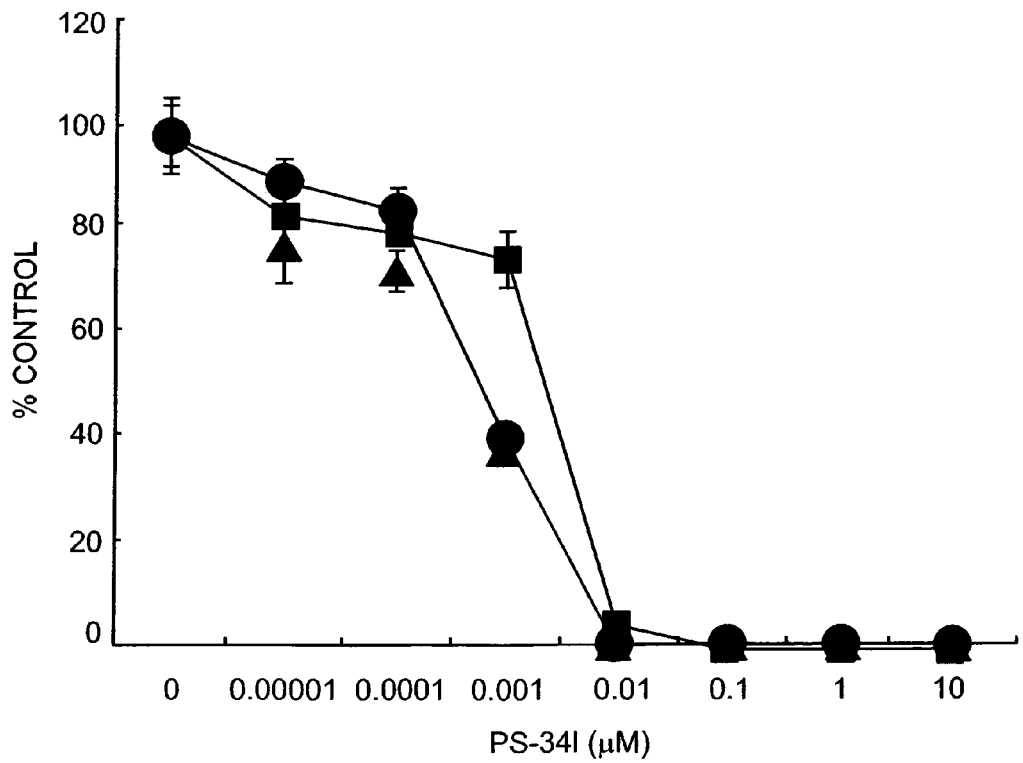
Figure 4A:
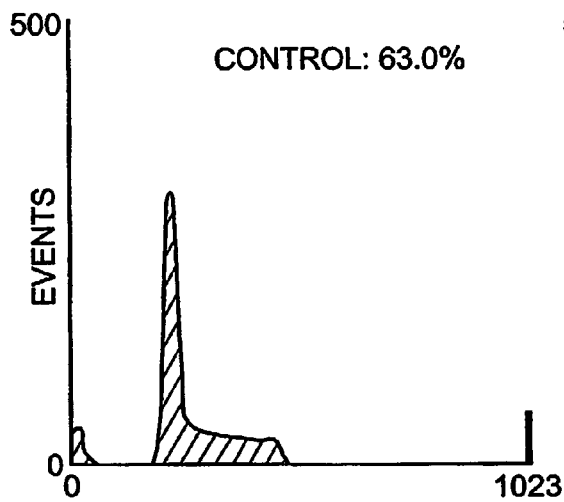
FIGS. 4A-4D show the effect of compound 1 on cell cycle profile. U266 cells were cultured in the presence of compound 1 (10 μM for 24, 36, and 48 h), harvested, stained with PI, and analyzed for cell cycle profile by flow cytometry. These results show that compound 1 induced G1 growth arrest, but not apoptosis, in U266 cells.
Figure 4B:
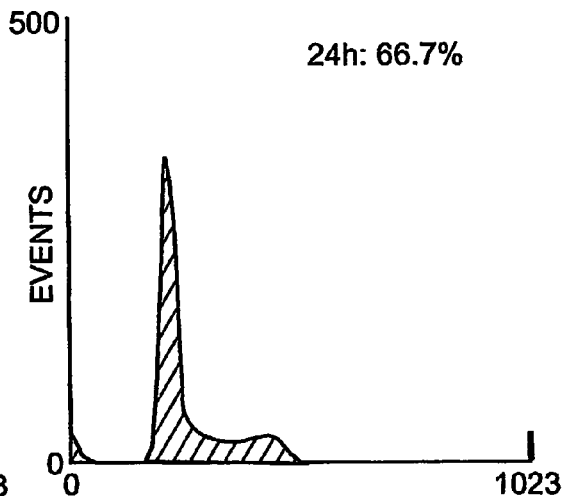
Figure 4C:
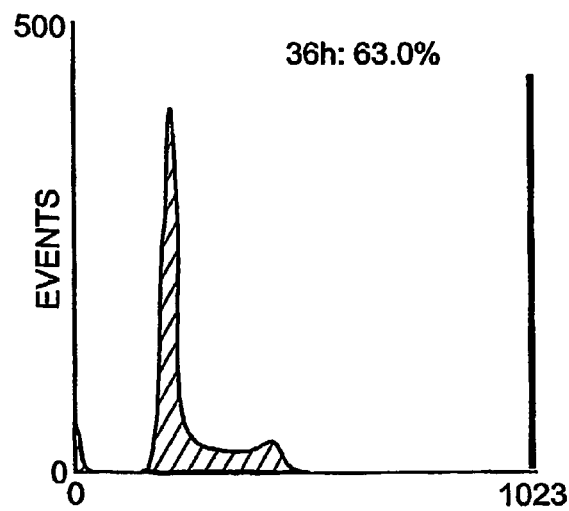
Figure 4D:
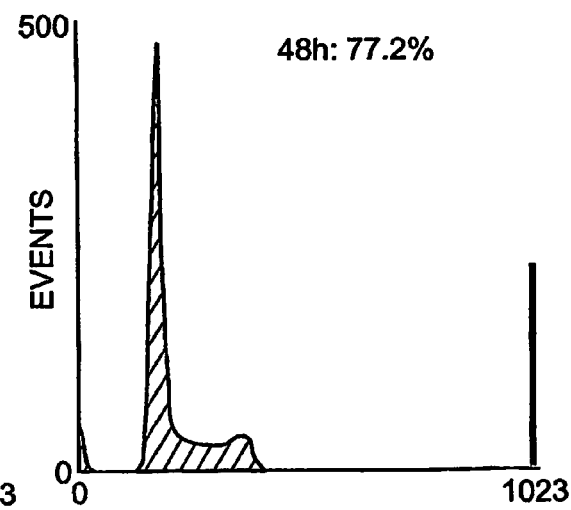

To study the direct effect of compound 1 on MM cells, [3H]-TdR uptake was measured in MM.1S, U266, and RPMI8226 cell lines cultured for 48 h in the presence of compound 1 (1.5-50 µM). Twenty % to 50% inhibition in proliferation was observed at dose >12.5 µM compound 1 (FIG. 3A). In contrast, PS-341 completely inhibited [$^3$H]-TdR uptake in all cell lines tested at IC50 of 0.02-0.005 (FIG. 3B). These results indicate that complete blockade of NF-κB activation cannot achieve >50% inhibition of DNA synthesis in MM cell lines, and that complete inhibition by PS-341 is mediated through inhibition of another signaling pathway, such as p42/44 MAPK (Ogata et al., *J. Immunol.* 159:2212 (1997)).

Cell cycle profile, assessed by PI staining, was also examined in these MM cell lines. Interestingly, compound 1 induced G1 growth arrest, but not apoptosis, in U266 cells (FIG. 4). Similar results were observed in RPMI8226 cells (data not shown). These data show that NF-κB blockade induces G1 growth arrest in MM cells.

Example 7

Compound 1 Does Not Affect Phosphorylation of p42/44 MAPK or STAT3 in MM.1S Cells As can be seen in FIG. 5, IL-6 induces phosphorylation of both p42/44 MAPK and STAT3 in MM.1S cells, and the MEK1 inhibitor PD98059 selectively inhibits p42/44 MAPK phosphorylation. PS341 also inhibits p42/44 MAPK phosphorylation; however, compound 1 does not inhibit either p42/44 MAPK or STAT3 phosphorylation. Phosphorylation of Akt triggered by IL-6 was also unaffected by compound 1 pre-treatment (data not shown). These results indicate that compound 1 specifically blocks NF-κB, without affecting other known signaling pathways in MM.1S cells triggered by IL-6.

Example 8

Dex Upregulates IκBα Protein and Enhances the Inhibitory Effect of Compound 1 on NF-κB Activation in MM.1S Cells MM.1S cells were cultured in the presence of Dex (1 µM for 0-36 h), and expression of IκBα protein was assessed by Western blotting. As can be seen in FIG. 6A, Dex significantly induces IκBα expression, and IL-6 partially blocks Dex-induced upregulation of IκBα. NF-κB activation was next examined in the presence of Dex, with or without IL-6. TNFα induced activation of NF-κB in MM.1S cells is abrogated by pre-treatment with Dex (FIG. 6B). compound 1 also inhibits NF-κB activation triggered by TNFα in MM.1S cells in a dose-dependent fashion, and pre-treatment with Dex enhances the inhibitory effect of compound 1 (FIG. 6C). These results suggest that Dex inhibits NF-κB activation via upregulation of IκBα, with related G1 growth arrest and apoptosis.

Figure 7:
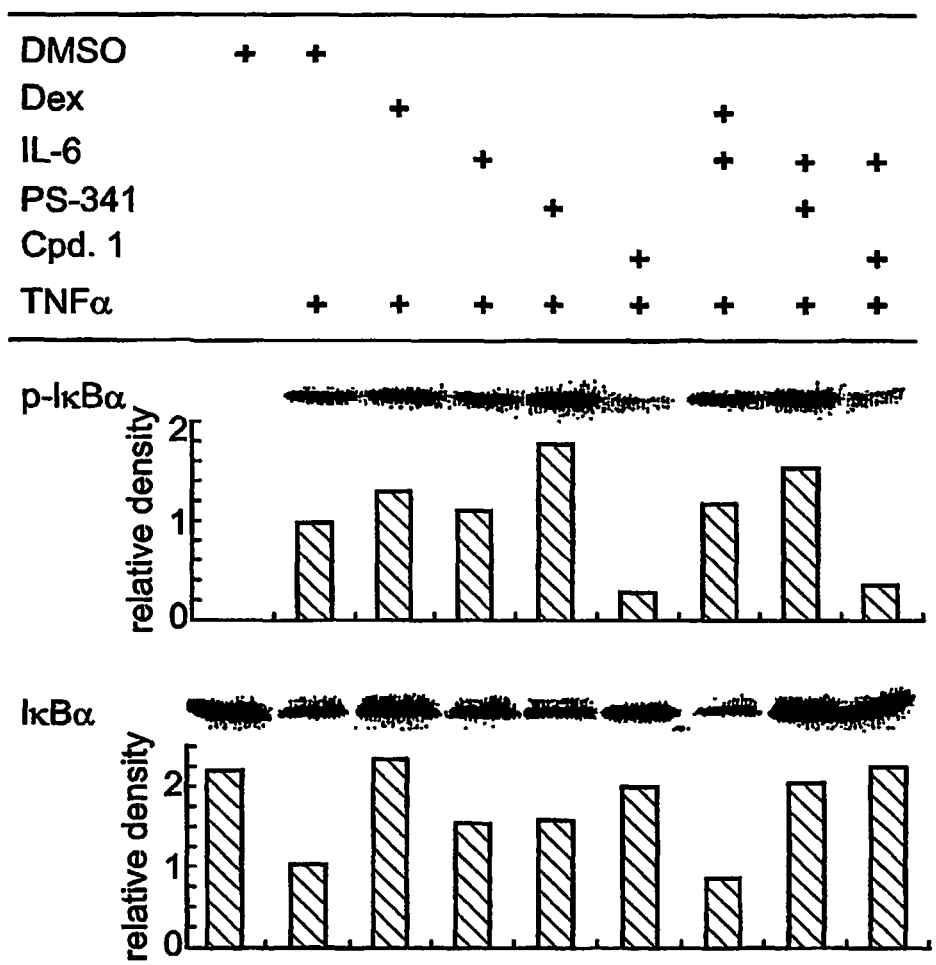
FIG. 7 is an immunoblot showing the effect of Dex, compound 1, PS 341 and/or IL-6 on TNFα-induced phosphorylation of IκBα. MM.1S cells were cultured in the presence of Dex (1 μM for 18 h), IL-6 (50 ng/mL for 18 h), PS341 (5 μM for 60 min) or compound 1 (10 μM for 90 min), and then stimulated by TNFα (5 ng/mL for 5 min). The cells were harvested, lysed, electrophoresed, and then immunoblotted with anti-phospho-IκBα and anti-IκBα Abs. These results show that IL-6 does not affect IκBα phosphorylation triggered by TNFα.

The effect of Dex, compound 1, PS-341 and/or IL-6 on TNFα induced phosphorylation of IκBα in MM.1S cells was next examined. As can be seen in FIG. 7, Dex, PS-341 and/or IL-6 does not inhibit TNFα-induced phosphorylation of IκBα; moreover, PS-341 enhances phosphorylation of IκBα, due to inhibition of proteasome activity and accumulation of IκBα. In contrast compound 1, in the presence or absence of IL-6, inhibits phosphorylation of IκBα. Dex inhibits TNFα-induced degradation of IκBα, whereas IL-6 blocks this effect. Both PS-341 and compound 1 inhibit degradation of IκBα, in the presence or absence of IL-6.

Example 9

Growth Inhibitory Effect of Compound 1 in the Presence of Dex and/or IL-6 in MM

Figure 8A:
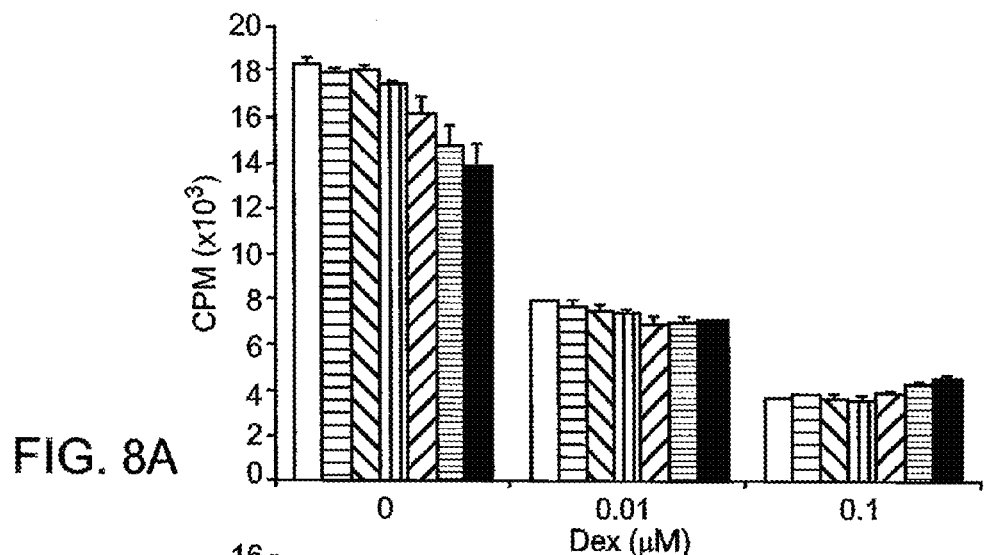
FIG. 8 is a graphical representation of the effect of compound 1 on cell growth. (A) MM.1S cells were cultured with DMSO control (□), or with 1.5 μM (▣), 3 μM (◨), 6 μM (▥), 12.5 μM (▨), 25 μM (▤), and 50 μM (■) compound 1, in the absence or presence of 0.01 and 0.1 μM Dex for 48 h. (B) MM.1S cells were cultured with DMSO control (□), or with 1.5 μM (▨), 3 μM (▣), 6 μM (◨), or 12.5 μM (■) compound 1, in the absence or presence of 0.5, 5, and 50 ng/mL IL-6 for 48 h. (C) MM.1S cells were cultured with DMSO control (□), or 0.4 μM (◨), 2 μM (▨), or 10 μM (■) compound 1 in the presence of Dex (0.1 μM) and/or IL-6 (50 ng/mL) for 48 h. DNA synthesis was assessed by [$^3$H]-TdR uptake. These results show that compound 1 inhibits growth and blocks the protective effect of IL-6 against Dex-induced growth inhibition.
Figure 8B:
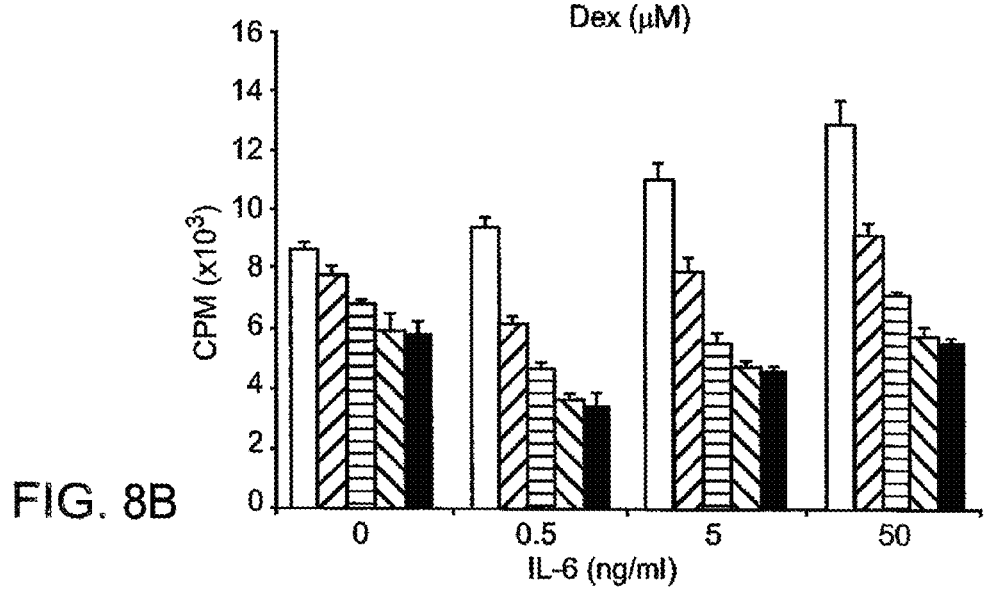
Figure 8C:
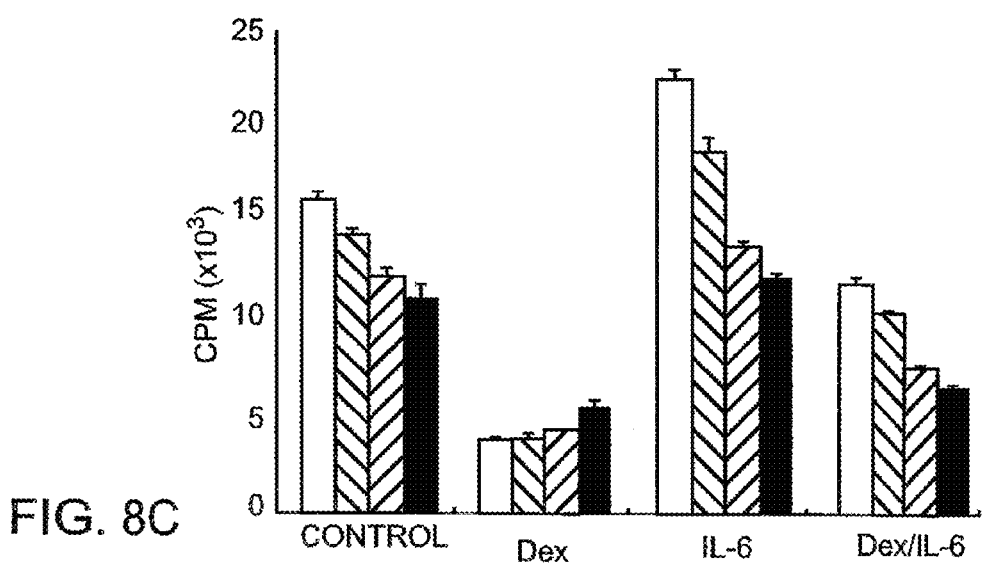

As can be seen in FIG. 8A, Dex inhibited IL-6 induced proliferation of MM.1S cells, but compound 1 did not enhance its effect. Importantly, both constitutive and IL-6 induced DNA synthesis in MM.1S cells was abrogated in the presence of compound 1 in a dose dependent fashion (FIG. 8B). Furthermore, the protective effect of IL-6 on Dex-induced growth inhibition was also abrogated by compound 1 (FIG. 8C). These data suggest that promotion of cell growth and survival by IL-6 is mediated, at least in part, via NF-κB signaling pathway.

Figure 9A:
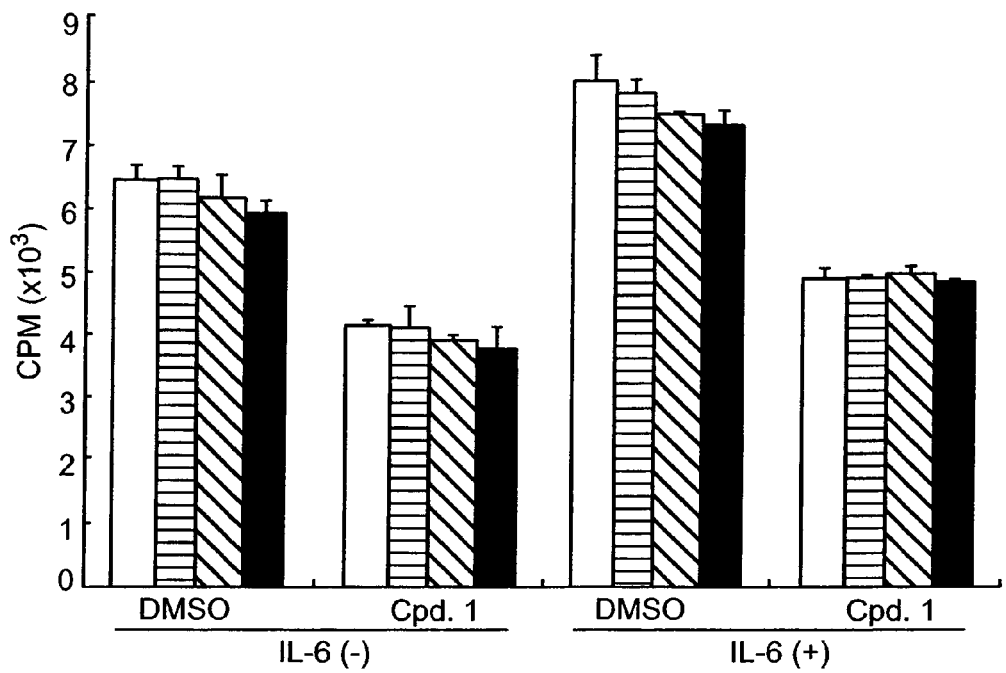
FIG. 9 is a graphical representation of the effect of compound 1 on cell growth in cells treated with the immunomodulatory derivative IMiD3 in the presence or absence of IL-6. (A) MM.1S cells were cultured for 48 h with DMSO control (□), or with 25 μM (▣), 50 μM (◨), or 100 μM (■) thalidomide (Thal), in the presence or absence of compound 1 (10 μM) and with or without IL-6 (50 ng/mL). (B) MM.1S cells were cultured for 48 h with DMSO control (□), or with 0.25 μM (▣), 0.5 μM (◨), or 1 μM (■) IMiD3, in the presence or absence of compound 1 (10 μM) and with or without IL-6 (50 ng/mL). DNA synthesis was assessed by [$^3$H]-TdR uptake. these results show that compound 1 overcomes the protective effect of IL-6 against IMiD3.
Figure 9B:
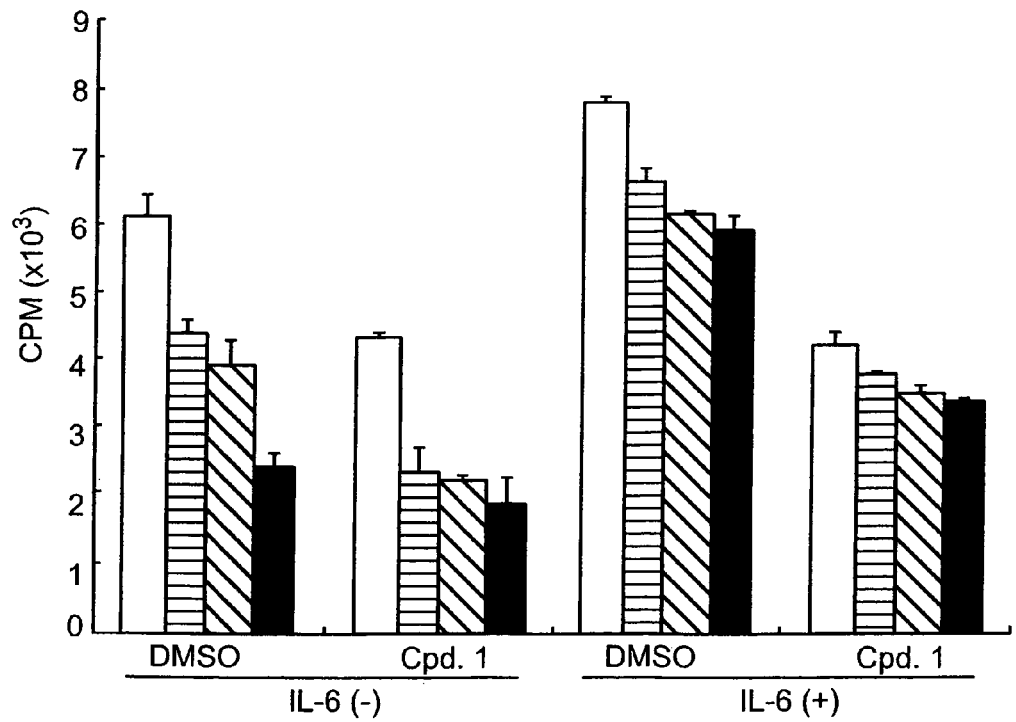

Thalidomide (Thal) and its immunomodulatory derivative (IMiD3) previously have been reported to inhibit MM.1S cell growth and that IL-6 abrogates this IMiD effect (Hideshima et al. *Blood* 96:2943 (2000)). Therefore, the effect of compound 1 on DNA synthesis of MM.1S cells treated with Thal and IMiD3 was studied in the presence or absence of IL-6. As can be seen in FIG. 9, IMiD3 significantly (p<0.001) inhibited DNA synthesis in MM.1S cell in a dose dependent fashion (0.25-1 µM). IL-6 (20 ng/mL) overcomes the effect of IMiD3; importantly, however, compound 1 neutralized the inhibitory effect of IL-6 against IMiD3. These studies suggest that NF-κB blockade can overcome resistance to Thal/IMiDs.

Example 10

Compound 1 Inhibits TNFα-Induced ICAM-1 Expression on MM Cells

Figure 10A:
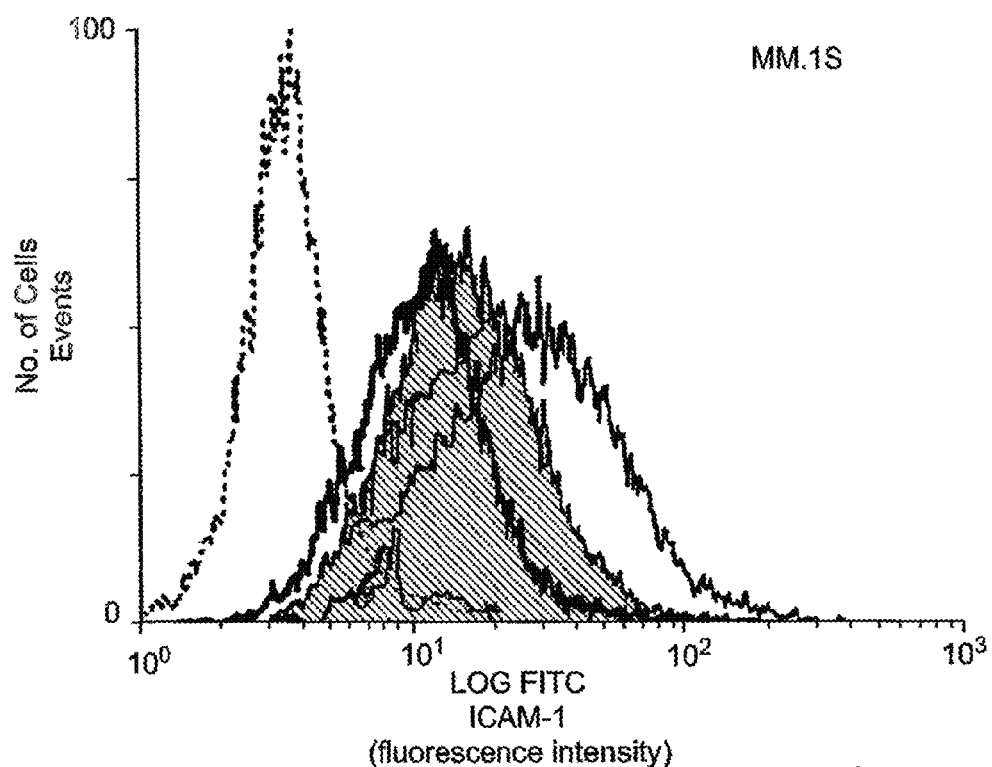
FIGS. 10A-10B show the effect of compound 1 on TNFα-induced ICAM-1 expression on MM cells. MM.1S and RPMI8226 cells were cultured for 24 h with DMSO control (_), TNFα (5 ng/mL) alone (_), or TNFα+compound 1 ( ). The cells were harvested, stained with isotype control ( . . . ) or FITC-conjugated anti-ICAM-1 Ab, and analyzed using flow cytometry. These results show that compound 1 inhibits TNF-α-induced ICAM-1 expression on MM cells.
Figure 10B:
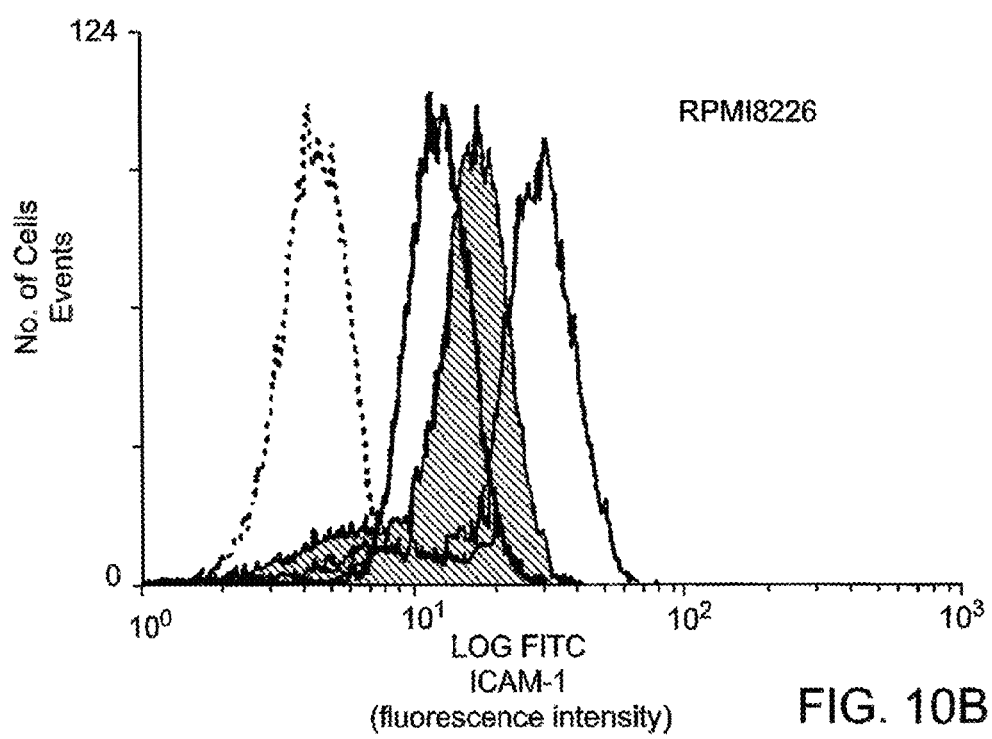

TNFα has been shown to induce ICAM-1 and VCAM-1 expression on both BMSCs and MM cells, and the proteasome inhibitor PS-341 blocks induction of these molecules (Hideshima et al., *Cancer Res.* 61:3071 (2001)). Since PS-341 is not a specific NF-κB inhibitor, it cannot be concluded from these studies that TNFα-induced upregulation of ICAM-1 and VCAM-1 is mediated through NF-κB. However, as can be seen in FIG. 10, compound 1 also inhibits TNFα-induced upregulation of ICAM-1 expression on MM.1S and RPMI8226 cells. This result strongly suggests that upregulation of ICAM-1 by TNFα is mediated via activation of NF-κB.

Example 11

TNFα and Compound 1 Triggers Apoptosis in MM.1S Cells

Figure 11:
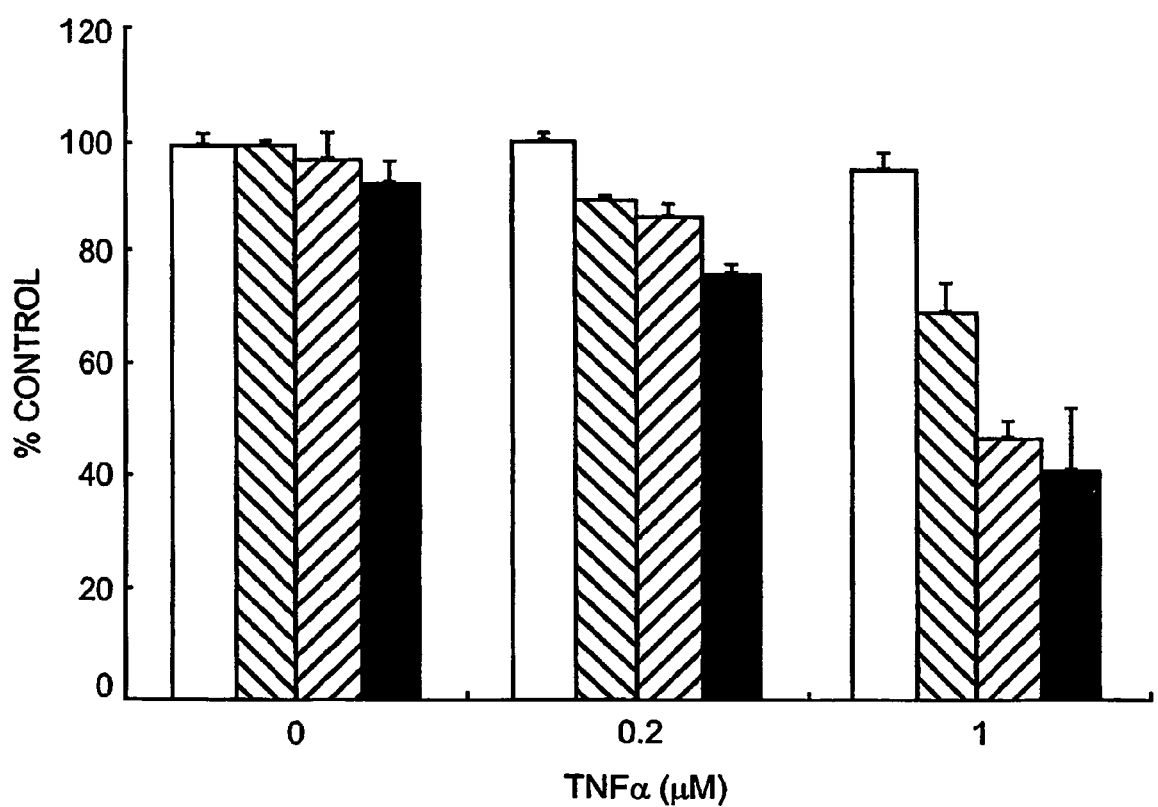
FIG. 11 shows that TNFα induces apoptosis in MM.1S cells treated with compound 1. MM.1S cells were cultured for 48 h with 0.2 and 1 ng/mL TNFα, in the absence (□) or presence of 2.5 μM (◨), 5 μM (▨), 10 μM (■) compound 1. Cell viability was assessed by MTT assay.

TNFα induces modest proliferation, but not apoptosis, in MM.1S cells (Hideshima et al., *Oncogene* 20:4519 (2001)). To test the hypothesis that TNFα would induce apoptosis in MM.1S cells when NF-κB activation is blocked by compound 1, MM.1S cells were cultured with TNFα, in the presence or absence of compound 1. As can be see in FIG. 11, TNFα treatment does not affect viability of MM.1S cells, assessed by MTT assay; however, in the presence of compound 1, viability of the cells was significantly decreased (p<0.001). For example, TNFα (1 ng/mL) induced 60% growth inhibition of MM.1S cells the presence of 10 µM compound 1. This effect on MM.1S viability is also confirmed by trypan blue exclusion (data not shown). These studies suggest that NF-κB mediates protection of MM.1S cells against TNFα-induced apoptosis.

Example 12

Effect of Compound 1 on Paracrine MM Cell Growth and IL-6 Secretion

Figure 12A:
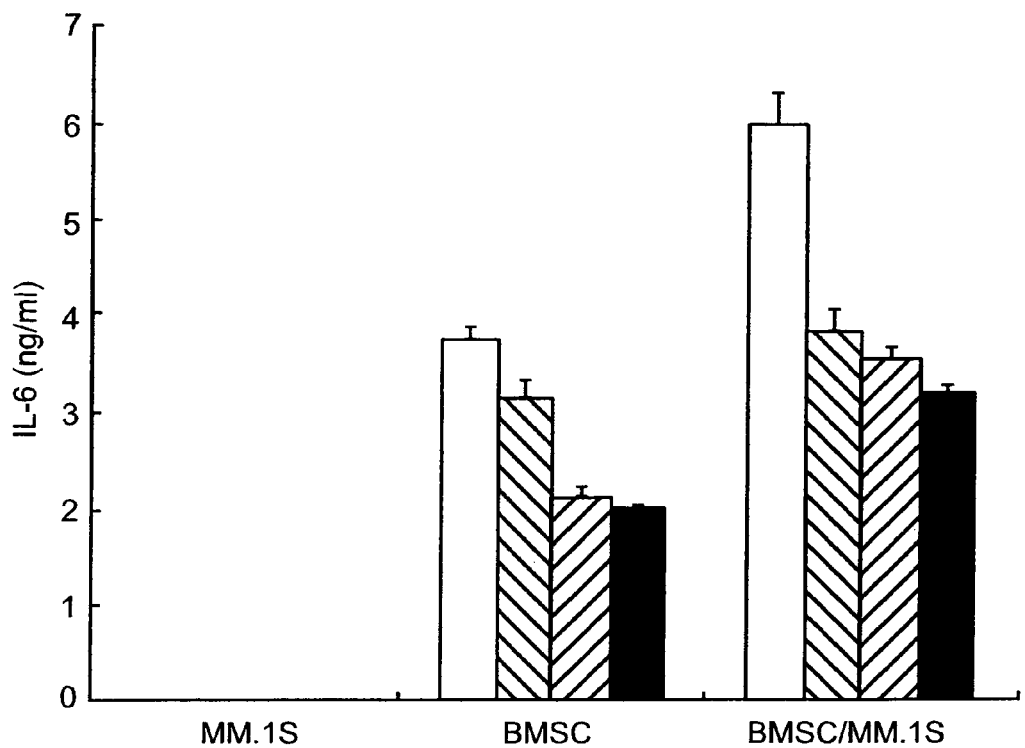
FIG. 12 shows that compound 1 inhibits paracrine MM cell growth and IL-6 secretion in BMSCs triggered by MM cell adherence. BMSCs, BMSCs with MM.1S cells, or MM.1S cells alone were cultured for 48 h, in the presence of DMSO control (□), or with 0.4 μM (◨), 2 μM (▨), or 10 μM (■) compound 1. (A) IL-6 level was measured in culture supernatants by ELISA, and (B) DNA synthesis was assessed by [$^3$H]-TdR uptake.
Figure 12B:
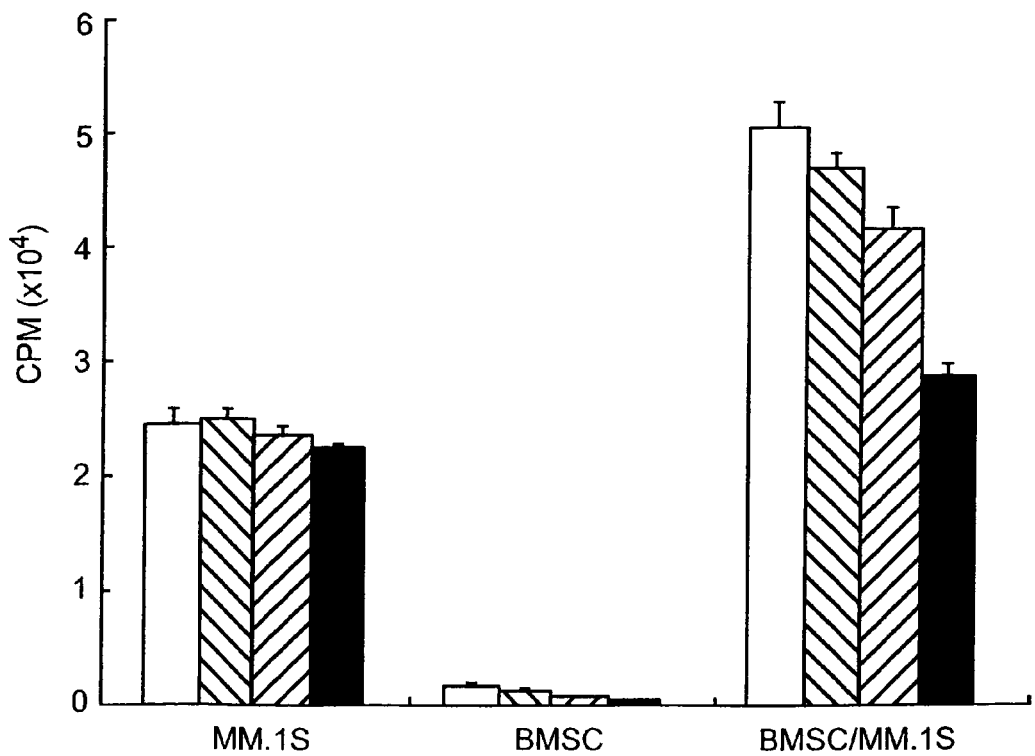

To study the role of NF-κB activation in regulating IL-6 transcription and secretion, as well as related paracrine MM cell growth in the BM milieu, MM.1S cells were cultured with or without BMSCs, in the presence or absence of compound 1. As can be seen in FIG. 12A, compound 1 blocks constitutive secretion of IL-6 in BMSCs in a dose dependent fashion. Importantly, adhesion of MM.1S cells to BMSCs triggers increased IL-6 secretion (1.6 fold, p<0.01), and compound 1 also blocks this response in a dose dependent fashion. Adherence of MM.1S cells to BMSCs also triggers increased MM.1S cell growth (1.9 fold), and compound 1 similarly inhibits this augmentation in a dose dependent fashion (FIG. 12B). These data confirm the hypothesis that induction of IL-6 secretion from BMSCs triggered by MM cell adhesion is mediated through NF-κB (Chauhan et al., *Blood* 87:1104 (1996)), and show that compound 1 can abrogate this effect.

EQUIVALENTS

While the foregoing invention has been described in some detail for purposes of clarity and understanding, it will be appreciated by one skilled in the art from a reading of this disclosure that various changes in form and detail can be made without departing from the true scope of the invention and appended claim.

What is claimed is:

1. A method for inhibiting multiple myeloma cell growth, comprising contacting a multiple myeloma cell with an effective amount of N-(6-chloro-9H-β-carbolin-8-yl)-nicotinamide or a stereoisomer or physiologically tolerable salt thereof.

2. The method of claim 1, wherein the multiple myeloma cell is in an animal.

3. The method of claim 2, wherein the animal is a mammal.

4. A method for treating multiple myeloma, comprising administering to a patient with multiple myeloma an effective amount of N-(6-chloro-9H-β-carbolin-8-yl)-nicotinamide or a stereoisomer or physiologically tolerable salt thereof.

* * * * *